United States Patent [19]

Pettit et al.

[11] Patent Number: 5,671,736
[45] Date of Patent: Sep. 30, 1997

[54] FETAL ELECTRODE PRODUCT WITH EASY-TO-HANDLE CONNECTOR

[75] Inventors: James Pettit, Landsdowne; Edward Dowd, Mallorytown, both of Canada; Richard A. Clement, Stratford, N.J.; Cleatis A. Eichelberger, Delran, N.J.; Kenard E. Urion, Woodbury, N.J.

[73] Assignee: Graphic Controls Corporation, Buffalo, N.Y.

[21] Appl. No.: 543,417

[22] Filed: Oct. 17, 1995

[51] Int. Cl.⁶ .................................................. A61B 5/0448
[52] U.S. Cl. ............................................................ 128/642
[58] Field of Search ................................... 128/642, 698; 607/127; 125/5 R

[56] References Cited

U.S. PATENT DOCUMENTS

| | | |
|---|---|---|
| Re. 28,990 | 10/1976 | Hon et al. . |
| Re. 32,294 | 7/1986 | Halvorsen . |
| 3,580,242 | 5/1971 | La Croix . |
| 3,800,800 | 4/1974 | Garbe et al. . |
| 3,827,428 | 8/1974 | Hon et al. . |
| 3,910,271 | 10/1975 | Neward . |
| 4,080,961 | 3/1978 | Eaton . |
| 4,149,528 | 4/1979 | Murphy . |
| 4,180,080 | 12/1979 | Murphy . |
| 4,254,764 | 3/1981 | Neward . |
| 4,301,806 | 11/1981 | Helfer . |
| 4,320,764 | 3/1982 | Hon . |
| 4,321,931 | 3/1982 | Hon . |
| 4,353,372 | 10/1982 | Ayer . |
| 4,501,276 | 2/1985 | Lombardi . |
| 4,577,635 | 3/1986 | Meredith . |
| 4,644,957 | 2/1987 | Ricciardelli et al. . |
| 4,911,657 | 3/1990 | Berlin . |
| 4,913,151 | 4/1990 | Harui et al. . |
| 4,934,371 | 6/1990 | Malis et al. . |
| 5,012,811 | 5/1991 | Malis et al. . |
| 5,046,965 | 9/1991 | Neese et al. . |
| 5,062,426 | 11/1991 | Ulbrich et al. . |
| 5,104,388 | 4/1992 | Quackenbush . |
| 5,135,006 | 8/1992 | Bellinson . |
| 5,168,876 | 12/1992 | Quedens et al. . |
| 5,199,432 | 4/1993 | Quedens et al. . |
| 5,205,288 | 4/1993 | Quedens et al. . |
| 5,215,090 | 6/1993 | Hon et al. . |
| 5,373,843 | 12/1994 | Quedens et al. . |
| 5,388,579 | 2/1995 | Dowd et al. . |
| 5,423,314 | 6/1995 | Schmid . |

FOREIGN PATENT DOCUMENTS

| | | |
|---|---|---|
| 0092982 | 2/1983 | European Pat. Off. . |
| 0377432 | 11/1990 | European Pat. Off. . |
| 0484107A1 | 6/1992 | European Pat. Off. . |

OTHER PUBLICATIONS

Corometrics Medical Systems, Inc., Leg Plate for Use with Corometrics Model 115, 116 Fetal Monitors, as offered for sale in Catalog No. 2608DAO, Sep. 1988, 5 pages.

Primary Examiner—Lee S. Cohen
Attorney, Agent, or Firm—Ratner & Prestia

[57] ABSTRACT

A fetal electrode product for transmitting signals indicative of fetal heart rate from a fetus to a monitor. The product includes a slotted introducer which can be comfortably inserted through the cervix of the mother. A drive mechanism slides and rotates a holder—to which are attached, at opposite ends, a fetal spiral electrode (FSE) and a reference electrode—within the introducer to secure the FSE to the fetus. The solid drive mechanism has a drive rod, a handle on one end of the drive rod imparting translation and rotation to the drive rod, and a clutch on the opposite end of the drive rod imparting translation and rotation to the holder. The drive rod, handle, and clutch each have a channel transporting a twisted wire strand from the electrodes to a connector. The connector has an outside dimension greater than the inner diameter of the introducer to facilitate manipulation. The introducer cannot be pulled over the connector after the FSE is attached to the fetus; the wire strand exits the drive mechanism via its channel and the introducer through its longitudinal slot. A locking slit in the handle securely wedges the twisted wire strand in a fixed position before application of the FSE. A chamfer located at the intersection of the slot with the rearward end of the introducer also positions and helps wedge the twisted wire strand in a fixed position.

24 Claims, 17 Drawing Sheets

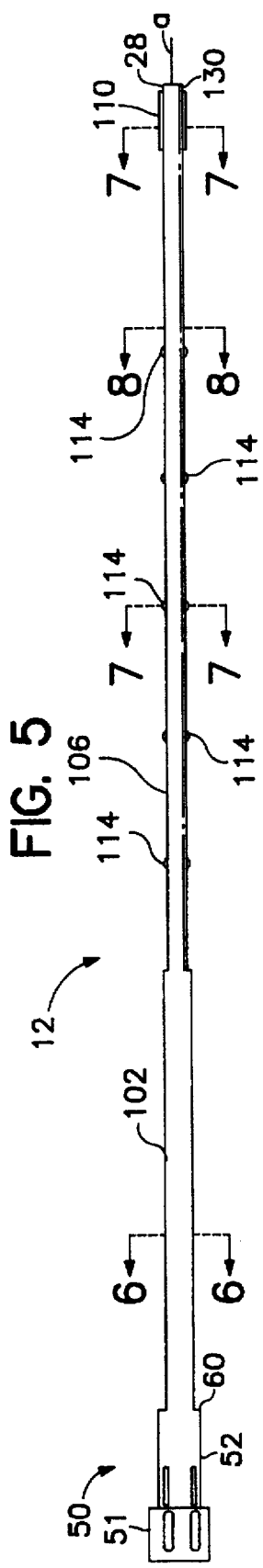
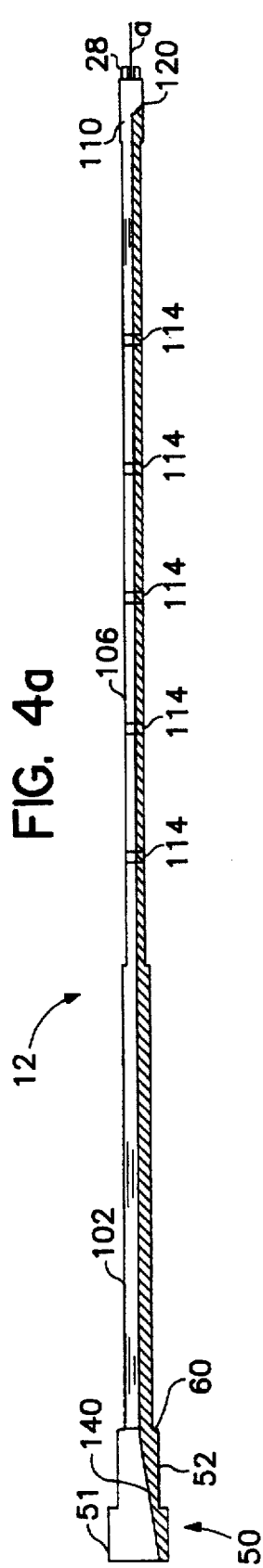
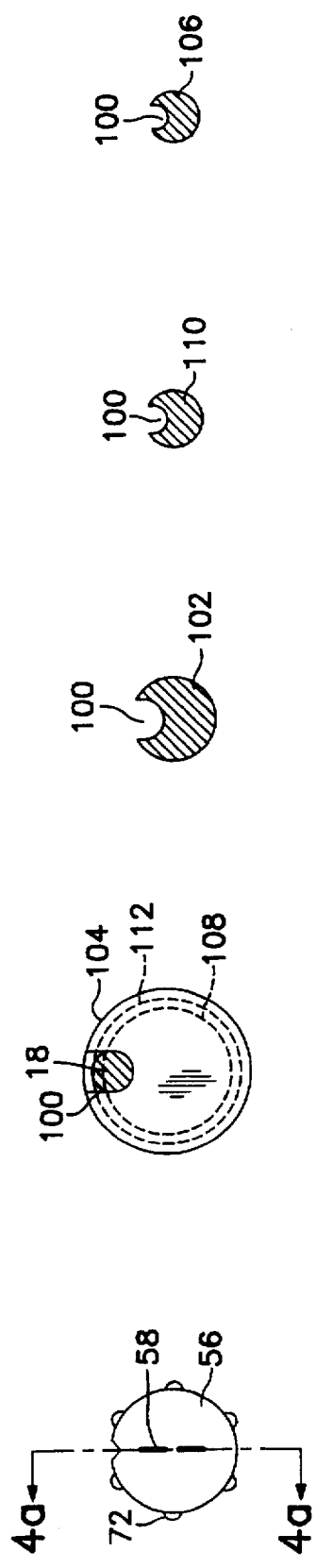

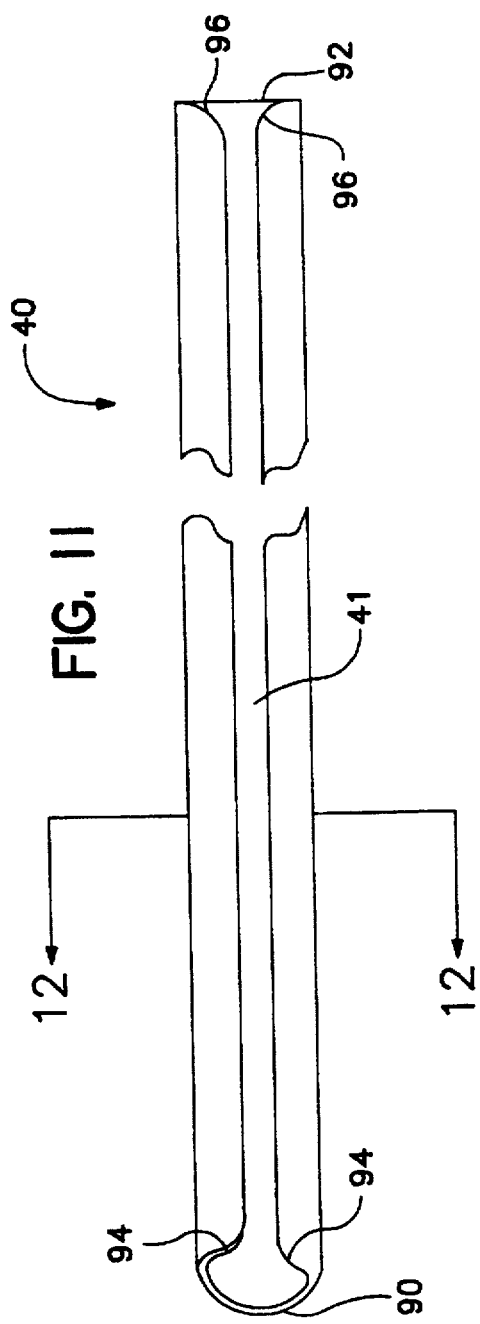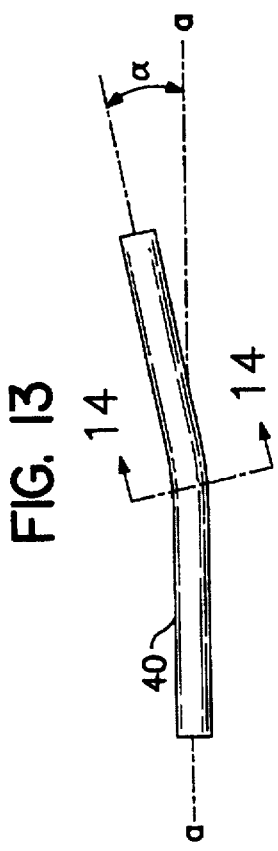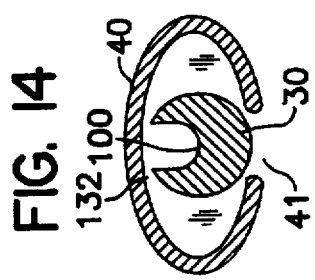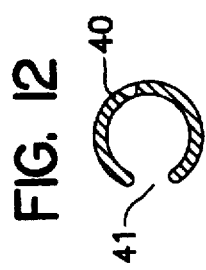

FETAL ELECTRODE PRODUCT WITH EASY-TO-HANDLE CONNECTOR

BACKGROUND OF THE INVENTION

1. Field of the Invention

The present invention relates to a fetal electrode and, in particular, to a fetal spiral electrode system including an introducer and a channeled drive mechanism for imparting the torque required to attach the electrode to the fetus.

2. Description of the Related Art

It is desirable to monitor fetal heart rate continuously during labor and delivery in order to detect fetal distress. Devices which are external to the mother's body are insufficiently sensitive and do not adequately isolate the fetal and maternal heartbeats. Consequently, devices which attach directly to the fetus during labor are used. U.S. Pat. No. Re. 28,990, issued to Hon et al., discloses a fetal spiral electrode (FSE) assembly commonly used to monitor fetal heart rate during birth.

The conventional fetal spiral electrode assembly includes a curved guide tube of adjustable shape for insertion of the fetal spiral electrode through the mother's cervix and into contact with the fetus during labor. A plastic tip or holder is slidably received in the guide tube. A sharp, pointed, fetal spiral electrode is mounted on the forward end of the holder for contacting the fetal epidermis.

A reference (maternal) electrode in the form of a flat fin or plate is electrically isolated from the fetal electrode and located on the rear end of the holder. A flexible, hollow drive tube with a cutout on its forward end fits inside the guide tube and engages the holder. The cutout of the drive tube engages the reference electrode in the holder to impart translation and rotation to the holder and, hence, to the fetal spiral electrode. A handle on the opposite end of the drive tube allows the user to push, pull, and rotate the drive tube within the guide tube. A forward-twisting force is applied to the drive tube to affix the fetal spiral electrode in the fetal epidermis.

The two electrodes are connected to separate wires, which are threaded through the common center of the drive and guide tubes until they ultimately exit at the rearward end of the drive tube. After the fetal spiral electrode is secured to the fetal epidermis, the drive tube and guide tube are removed by pulling the tubes longitudinally over the wires and away from the mother. Removal of the drive and guide tubes leaves the electrodes, the holder, and the wires in place inside the mother. The uninsulated ends of the wires opposite the electrodes are then connected to a fetal monitor.

Manual connection of the uninsulated ends of the wires is cumbersome and risks shorting the wires. If shorted, the wires cannot transmit correct signals from the fetal and reference electrodes. Accordingly, a connector can be added to the fetal spiral electrode assembly disclosed in the '990 patent. As taught by U.S. Pat. No. 5,205,288 (issued to Quedens et al.); U.S. Pat. No. 5,199,432 (issued to Quedens et al.); U.S. Pat. No. 5,168,876 (issued to Quedens et al.); and U.S. Pat. No. 5,373,843 (issued to Quedens et al.), the connector solves the problem of manual connection of the uninsulated ends of the wires. Because the drive and guide tubes are removed by pulling them longitudinally over the wires and connector, however, the connector must have an outer dimension which is smaller than the inside diameter of the drive tube and, of course, the larger diameter guide tube as well).

The wire connected to the fetal spiral electrode and the wire connected to the reference electrode form a twisted wire strand which enters the connector through a strain relief element. The wire from the fetal spiral electrode is connected to a first, gold, terminal or ring contact; the wire from the reference electrode is connected to a second, gold, terminal or ring contact. The terminals are electrically and physically separated by a spacer. The connector has a forward tapered tip.

The connector engages a support plate, which is affixed to the expectant mother (typically to the thigh) and provided to support the connector. Upon insertion of the connector into an opening of the support plate, the two ring contact terminals on the connector click into physical and electrical contact with two corresponding barrel contacts in the support plate. Moreover, the tip of the connector abuts a wall in the support plate to prevent over-insertion of the connector.

The support plate carries its own ground electrode. Consequently, three electrical circuit paths are created upon engagement of the connector with the support plate: (a) fetal electrode to a first wire to a first contact terminal to a first barrel contact to a first output terminal to the monitor; (b) reference electrode to a second wire to a second contact terminal to a second barrel contact to a second output terminal to the monitor; and (c) ground electrode to a third output terminal to the monitor.

To use the fetal spiral electrode product having a connector, the shape of the guide tube is adjusted and the guide tube is inserted through the mother's cervix and into contact with the fetus. Care must be exercised to assure that the sharp fetal spiral electrode does not extend out of the guide tube during insertion; otherwise, risk to the patient and fetus of injury and infection arises. Once the guide tube contacts the fetus (and is held against the fetus by one of the user's hands), the drive tube is advanced (using the second hand) until the fetal spiral electrode contacts the fetus.

While pressure is maintained against the fetus by the guide tube and drive tube, the drive tube is rotated, using the second hand and the handle, until the fetal spiral electrode is secured to the fetal epidermis. Typically, one full revolution suffices to secure the fetal spiral electrode. Then the drive tube and guide tube are removed, leaving the electrodes, the holder, and the wires in place inside the mother, by sliding them over the electrode wires and connector. Finally, the connector is plugged into the support plate.

The connector must be fully inserted into the support plate to assure optimal signal quality. The connector of the conventional device has a constant diameter along its length. The device cannot provide any visual assurance, therefore, that the connector has been fully inserted. This is one drawback of the conventional device.

A second drawback or problem associated with the conventional fetal spiral electrode assembly is that the electrode wires must be straightened completely before the guide and drive tubes are pulled over the wires and connector. Otherwise, the wires may drag, catch, or snag on the drive tube, as it is removed, placing tension on the fetal spiral electrode. Such tension may pull the fetal spiral electrode out of engagement with the fetus.

Another problem associated with the conventional fetal spiral electrode assembly is that the wires and the connector, which convey the electrical signal from the fetus to the monitor, must traverse laterally through the common, hollow center of the drive tube and guide tube. This means that the connector necessarily must have an outer dimension smaller than the internal diameter of the guide and drive tubes. Because the guide and drive tubes must be small in diameter in order to transit the closed cervix, this, in turn, means that the connector diameter must be relatively small.

The requirement of a small-diameter connector has several disadvantages. First, the clinician must grasp and handle the connector to insert it into the corresponding socket of the support plate. The smaller the connector, the more difficult it is to handle. Second, a proper connection of the connector to the support plate must be ensured. A smaller connector of constant cross-section is unable to provide assurance that the required connection has been achieved. Finally, the support plate and fetal spiral electrode operate in a fluid-filled environment. A smaller connector risks an inadequate seal of the opening in the support plate into which the connector is inserted. Absent an adequate seal, fluid from the environment may enter the opening in the support plate and adversely affect the connector-socket electrical connection or the other electrical circuit paths discussed above.

U.S. Pat. No. 4,644,957 (issued to Ricciardelli et al.) recognizes the drawback, that the connector must necessarily be of a diameter smaller than the guide and drive tubes, characteristic of the conventional fetal spiral electrode assembly. The '957 patent solves that problem by placing the wires alongside a solid drive wrench (rather than inside an annular drive tube) and by providing a slotted guide with a C-shaped cross-section (as opposed to a solid, annular guide tube). The wires reside freely inside the guide and parallel to the drive wrench. Because the wires are of a smaller diameter than the width of the longitudinal slot in the guide (enabling the wires to exit the slot), they must either be wound in a spiral around the drive wrench or positioned in the guide away from the slot to retain them securely inside the guide. After the fetal spiral electrode is secured to the fetus, the drive wrench is pulled out of the guide. The guide is then withdrawn, in a similar manner, as the wires slip freely out of the longitudinal slot in the guide.

The solution presented by the '957 patent has its own difficulties. The wires must be sized so that they are smaller than the width of the longitudinal slot in the guide. Thus, the size of the wires is restricted and the wires may exit the slot prematurely. More important, the wires reside freely inside the guide and may affect rotation of the drive wrench; the wires may be caught by the edges of the walls adjacent to the slotted guide. The wires may also become entangled around the drive wrench, in the worst case, preventing both rotation and removal of the drive wrench. The risk of entanglement is especially great if the wires are purposefully wound in a spiral around the drive wrench. Finally, the wires may not be aligned with the slot, after the drive wrench is removed, rendering withdrawal of the guide difficult.

As an alternative solution, Graphic Controls Canada Limited marketed a fetal ECG electrode product during the mid 1980's in Canada, under the MEDI-TRACE® trademark, which incorporated a channeled drive rod to eliminate routing of the wires through a hollow drive tube. The open channel in the drive rod provided for a clean release of the electrode wires after attachment of the fetal spiral electrode, thus reducing wire friction and tugging during removal of the drive rod.

The product was unsuccessful, in part, because the solid, channeled drive rod was inflexible (too rigid and stiff) in comparison to its hollow tube counterpart. The stiffness of a drive rod in a fetal spiral electrode assembly must balance competing requirements. The stiffness must be sufficient to (a) transmit torque directly from the handle to the holder and fetal spiral electrode, (b) provide the "feel" required to assure that the fetal spiral electrode is attached to the fetus without over-rotation which would risk damage to the fetal scalp, and (c) allow sufficient bend so that the fetal spiral electrode can be inserted comfortably into the mother.

In U.S. Pat. No. 5,388,579 (issued to Dowd et al.), a fetal electrode product having a solid, channeled drive rod is disclosed for transmitting signals indicative of fetal heart rate from a fetus to a monitor. The product has a drive mechanism which slides inside an annular guide tube and rotates the holder to secure attachment of the fetal spiral electrode to the fetus. The drive mechanism has (a) a solid drive rod with at least two regions of different diameter defining the torque versus angular deflection characteristics of the drive rod, (b) a handle connected to the drive rod and imparting translation and rotation to the drive rod, and (c) a clutch connected to the drive rod and imparting translation and rotation to the holder. The drive rod, handle, and clutch are integrally molded together to form the drive mechanism. Each of the drive rod, handle, and clutch has a channel transporting the twisted wire strand from the electrodes to the connector.

The product includes an annular guide tube sized to be comfortably inserted through the cervix of a mother in labor. The connector has an outside dimension greater than the outside diameter of the drive rod to facilitate handling. The connector outer dimension must be smaller than the inside diameter of the annular guide tube, however, so that the guide tube can be pulled over the connector after the fetal spiral electrode is attached to the fetus. Thus, although the connector in this product could have an outside diameter greater than the outer diameter of the drive rod, the connector diameter is still limited to a dimension which permits it to slide within the guide tube.

SUMMARY OF THE INVENTION

The present invention provides a fetal electrode product for transmitting signals indicative of a fetal heart rate from a fetus inside a mother to a monitor external to the mother. The product has a holder made of an insulating material to which are attached, at opposite ends, a fetal spiral electrode and a maternal reference electrode. A twisted wire strand includes a pair of wires respectively connecting the fetal spiral electrode and the maternal reference electrode to a connector. The twisted wire strand may include an untwisted length to facilitate removal of the fetal spiral electrode from the fetus.

The product also includes a slotted introducer which can be comfortably inserted through the cervix of the mother. The introducer has a longitudinal slot disposed along its entire length. The forward end of the introducer, which contacts the fetus, has a chamfer to help prevent harm or injury to the fetus and maternal tissue. The rearward end of the introducer may also be chamfered.

A drive mechanism slides and rotates the holder within the introducer to secure attachment of the fetal spiral electrode to the fetus. The drive mechanism has (a) a solid drive rod, (b) a handle connected to the drive rod and imparting translation and rotation to the drive rod, and (c) a clutch connected to the drive rod and imparting translation and rotation to the holder. The drive rod, handle, and clutch are integrally molded together to form the drive mechanism. Each of the drive rod, handle, and clutch has a channel transporting the twisted wire strand from the electrodes to the connector and, in turn, to the monitor.

The handle of the drive rod is provided with an incline under the channel for recessing the twisted wire strand. At the rearward end of the handle, at the deepest portion of the incline, a locking slit is provided in a plane transverse to the longitudinal axis of the drive mechanism. This slit engages the twisted wire strand such that tension is applied to the twisted wire strand to maintain the maternal electrode in engagement with the clutch. The locking slit keeps the twisted wire strand taut and within the channel of the drive mechanism throughout the process of attaching the fetal spiral electrode and thus prevents the twisted wire strand from catching on the slot of the introducer.

Disposed on either side of the channel in the rearward section of the handle are two substantially parallel raised wall portions which act as a tactile sensing member. This member helps the user to identify the radial direction in which to pull the electrode wires in order to disengage them from the locking slit. Therefore, the tactile sensing member permits a blind release of the electrode wires by sense of touch. The tactile sensing member can also be used as a pointer to inform the user when a complete rotation of the fetal spiral electrode has been achieved. The handle of the drive mechanism facing the forward end is also provided with a beveled shoulder. This feature helps to prevent the introducer from catching on the handle as the handle is rotated relative to the introducer.

The chamfer on the rearward end of the introducer can be used to position the twisted wire strand to facilitate wedging of at least one wire of the strand between the introducer and the drive rod. When the twisted wire strand is wedged, the fetal spiral electrode located on the end of the twisted wire strand is maintained in a retracted position and is protected within the introducer. The chamfered rearward end of the introducer also helps to prevent the slot of the introducer from catching on the handle upon rotation of the handle.

The connector has an outside dimension greater than the inner diameter of the introducer to facilitate manipulation. A shoulder ring substantially larger than the plug of the connector may be provided on the connector. Consequently, the introducer cannot be pulled over the connector after the fetal spiral electrode is attached to the fetus; the twisted wire strand exits the drive mechanism via its channel and the introducer through its longitudinal slot.

BRIEF DESCRIPTION OF THE DRAWING

The invention is best understood from the following detailed description when read in connection with the accompanying drawing, in which:

FIG. 3 is an end view of the first embodiment of the drive mechanism in accordance with the present invention;

FIG. 4a is a cross-sectional view taken along the line 4a—4a of FIG. 3;

FIG. 5 is a side view of the first embodiment of the present invention shown in FIGS. 3 and 4a;

FIG. 6 is a cross-sectional view taken along the line 6—6 of FIG. 5;

FIG. 7 is a cross-sectional view taken along either of the lines 7—7 of FIG. 5;

FIG. 8 is a cross-sectional view taken along the line 8—8 of FIG. 5;

FIG. 9 is a cross-sectional view of the drive rod of the first embodiment of the drive mechanism of the present invention, illustrating the three regions of varying diameter of the drive rod;

FIG. 10b is a magnified view of the chamfered or beveled handle of the drive mechanism shown in FIG. 10a;

FIG. 11 illustrates the slotted introducer of the present invention, as shown in FIG. 1, with optional chamfers shown on either end of the slotted introducer;

FIG. 12 is a cross-sectional view taken along the line 12—12 of FIG. 11;

FIG. 13 is a side view of the slotted introducer used in combination with the fetal spiral electrode system in accordance with the present invention, illustrating a typical bend angle;

FIG. 14 is a cross-sectional view taken along the line 14—14 of FIG. 13;

FIG. 19b is a top view of the tactile sensing member shown FIG. 19a.

DETAILED DESCRIPTION OF THE INVENTION

A. Overview of the Invention

Figure 1:
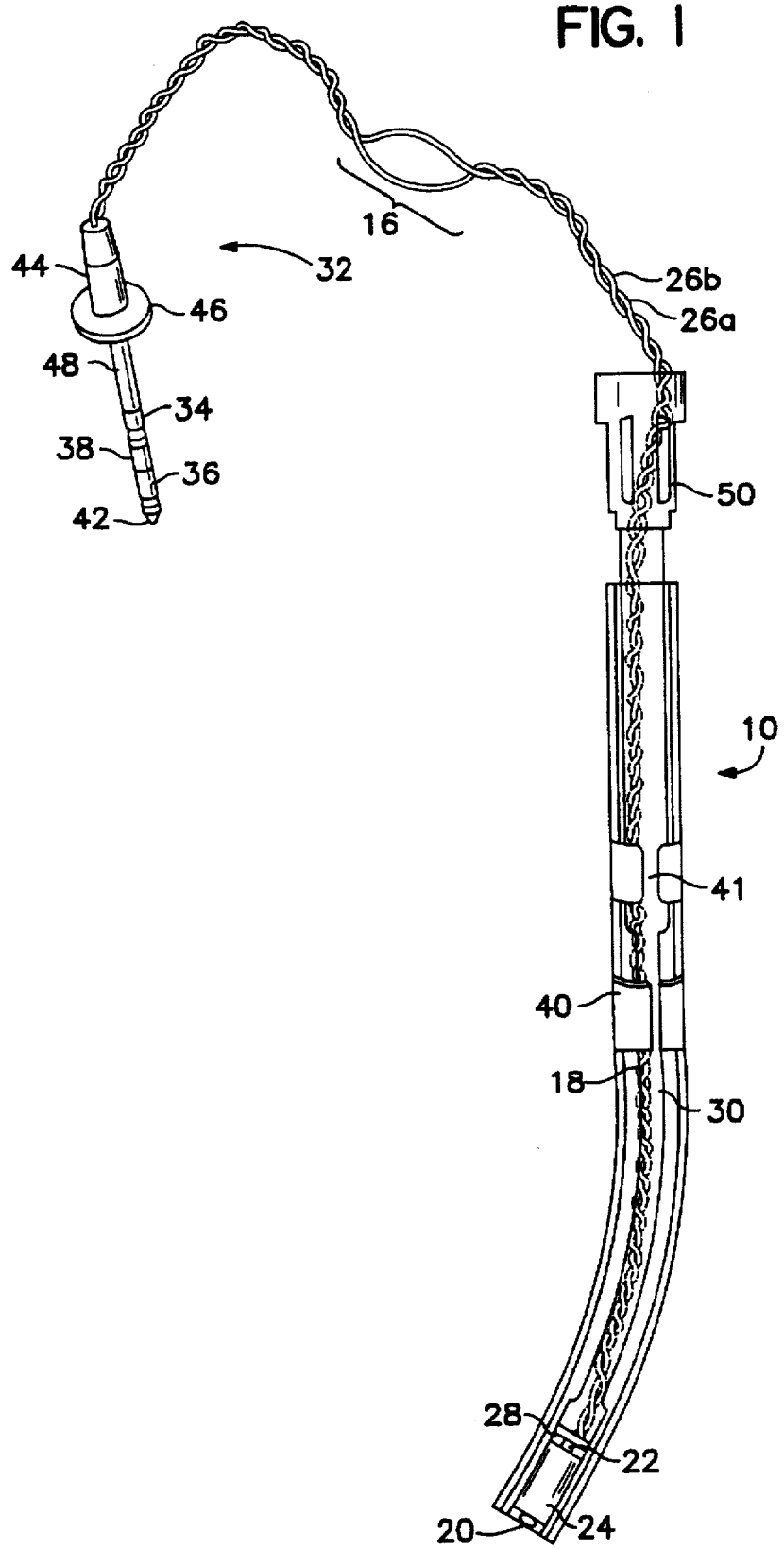
FIG. 1 is a side view of an exemplary fetal spiral electrode system in accordance with the present invention (with the slotted introducer shown in partial cross section)

Referring now to the drawing, wherein like reference numerals refer to like elements throughout, FIG. 1 is a side view of an exemplary fetal spiral electrode system 10 in accordance with the present invention. It is emphasized that the various components shown in the drawing are not to scale. On the contrary, the dimensions of the various components are arbitrarily expanded or reduced for clarity. Electrode system 10 includes a sharp, pointed fetal spiral electrode 20 for contacting the fetal epidermis; a reference (maternal) electrode 22 in the form of a flat fin or plate which is electrically isolated from fetal spiral electrode 20; a holder 24; and two electrode wires 26a and 26b.

Holder 24 is an electrically insulating plastic and is adapted to be slidably received inside an introducer 40. Introducer 40 has a longitudinal slot 41 to facilitate removal from wires 26a and 26b. Fetal spiral electrode 20 is mounted on the forward end of holder 24. Reference electrode 22 is attached to the rearward end of holder 24.

Figure 4B:
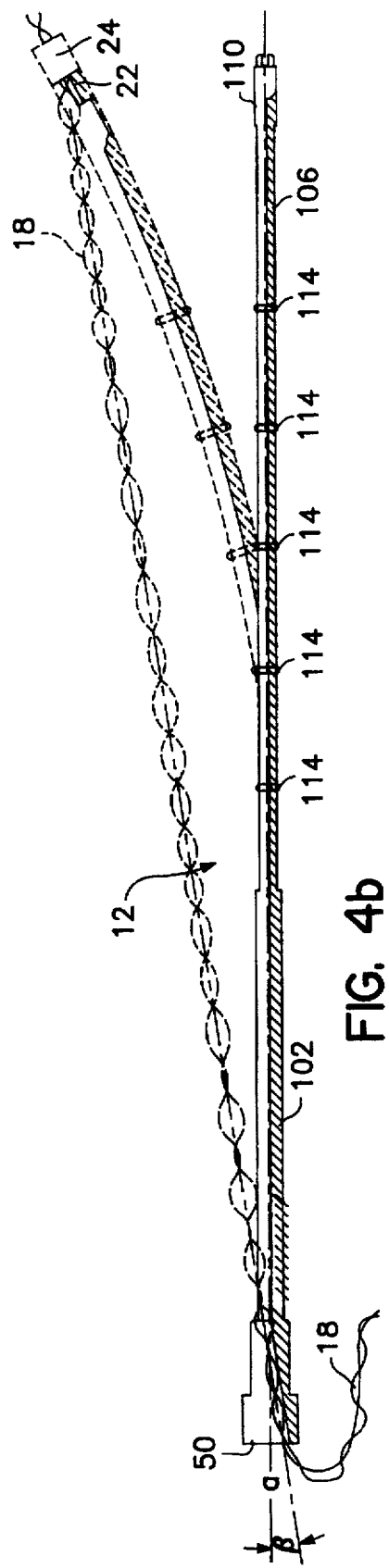
FIG. 4b is a side view of the drive mechanism of FIG. 4a as the electrode wires are loaded into the handle of the mechanism before inserting the drive mechanism into the slotted introducer.

An integral, flexible drive mechanism 12 is provided (see FIGS. 4a, 4b, and 5). Drive mechanism 12 includes a drive rod 30 which is slidably received in introducer 40 (see FIG. 1). Drive rod 30 has a clutch 28 at its forward end. Clutch 28 engages reference electrode 22 in holder 24 to impart translation and rotation to holder 24 and, hence, to fetal spiral electrode 20. A handle 50 on the opposite end of drive rod 30 allows the user to push, pull, and rotate drive rod 30. Drive rod 30, clutch 28, and handle 50 are integrally molded together to form drive mechanism 12 of fetal spiral electrode system 10.

Electrode wires 26a and 26b are separately coupled to respective electrodes 20 and 22. Electrode wire 26a (typically green in color) connected to fetal spiral electrode 20 and electrode wire 26b (typically red) connected to reference electrode 22 form a twisted wire strand 18 which extends from electrodes 20 and 22 along the entire length of drive rod 30 and handle 50. A longitudinal locking slit 58 (see FIG. 3) is provided in the end 56 of handle 50 opposite drive rod 30. Locking slit 58 locks wire strand 18 in a fixed position. The ends of wires 26a and 26b opposite holder 24 terminate in a connector 32.

Figure 2:
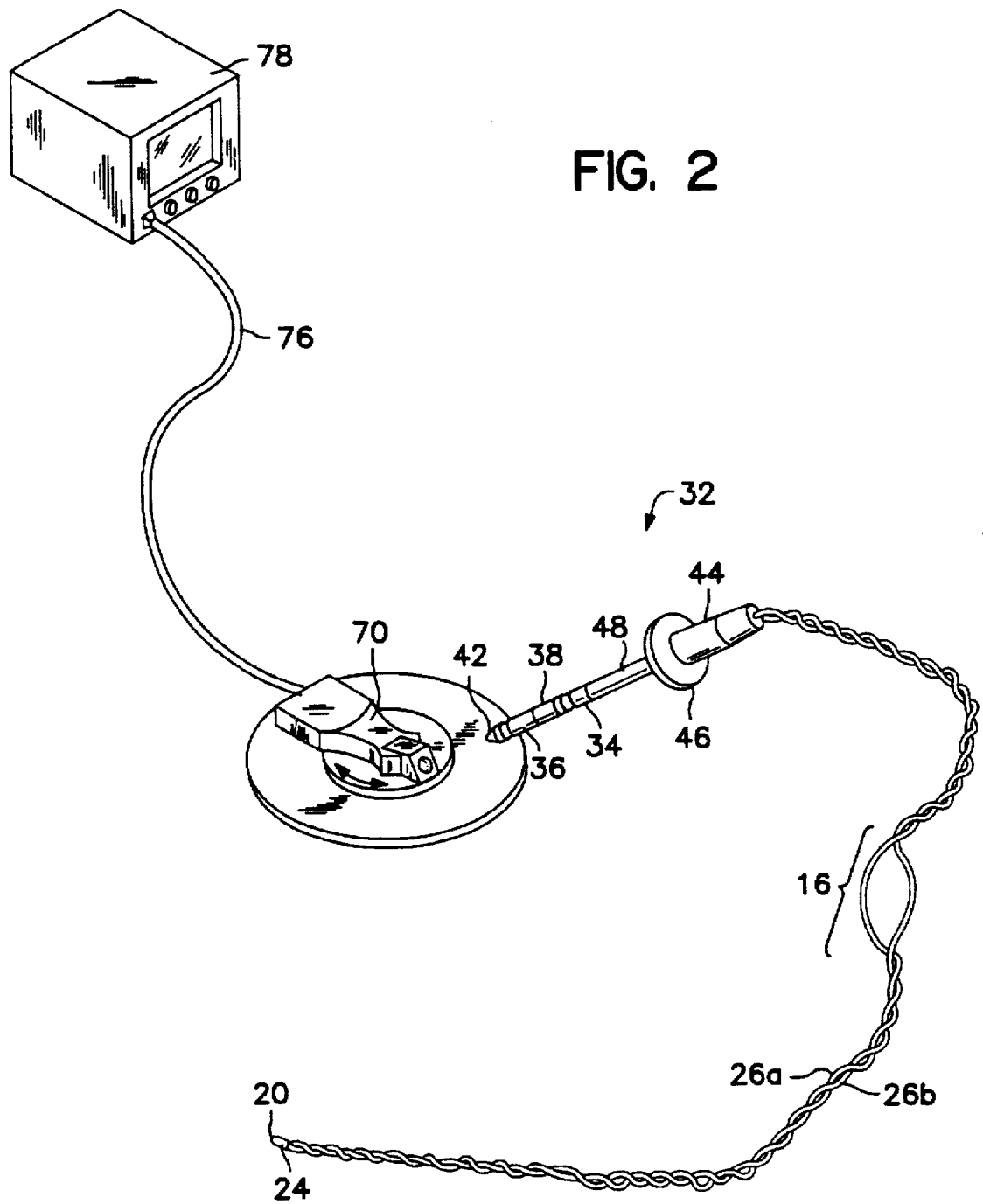
FIG. 2 is a perspective view of the improved electrode wires and connector of the present invention and illustrates those components in combination with several conventional elements.

Turning to FIG. 2, the individual wires 26a and 26b are separately connected to first and second terminal (or ring) contacts 34 and 36 in connector 32. Contacts 34 and 36 are electrically and physically separated by a spacer 38. Connector 32 is designed to be inserted into a support plate 70 which is affixed to the mother (typically to the thigh). Support plate 70 is connected, via a cable 76, to a monitor 78. Insertion of connector 32 in support plate 70 connects electrodes 20 and 22 to monitor 78.

B. Specific Components of the Invention

Having generally described fetal spiral electrode system 10, the individual components of fetal spiral electrode system 10 can now be described in greater detail.

1. The Electrode Wires

Each wire 26a and 26b is approximately 1 mm (0.04 inches) in diameter. The length of wires 26a and 26b from maternal electrode 22 and fetal spiral electrode 20, respectively, to connector 32 is about 610 mm (24 inches). This length allows the clinician sufficient "play" to choose placement of support plate 70 on the mother's abdomen or leg at a number of suitable positions.

As noted above and illustrated in FIG. 1, wires 26a and 26b form twisted wire strand 18. Wires 26a and 26b may (optionally) be provided with an untwisted length 16 along a short distance (25–50 mm or 1–2 inches) of wire strand 18. Untwisted length 16 may be located at any point between connector 32 and the point at which wires 26a and 26b engage locking slit 58 in handle 50.

To remove it from engagement with the fetus, fetal spiral electrode 20 must be rotated counterclockwise. Many clinicians pull wires 26a and 26b apart to facilitate removal of fetal spiral electrode 20 from the fetus. Absent untwisted length 16, the clinician may cut wires 26a and 26b before they are pulled apart. Untwisted length 16 allows the clinician to separate wires 26a and 26b without cutting them. Untwisted length 16 is provided, therefore, close to the point at which wires 26a and 26b engage locking slit 58 in handle 50. For example, untwisted length may be 180–230 mm (7–9 inches) from connector 32.

Figure 18:
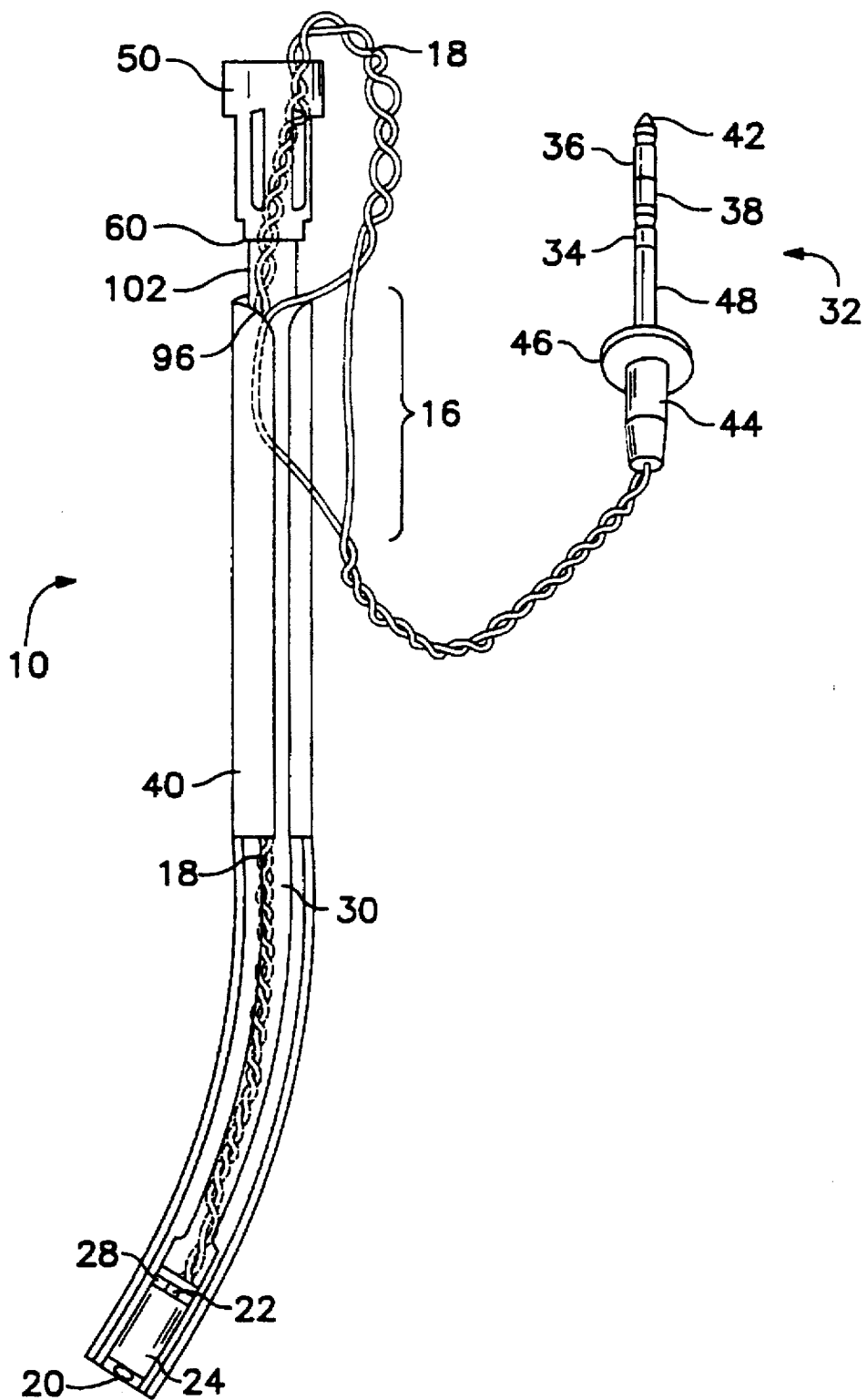
FIG. 18 is a side view of an exemplary fetal spiral electrode system of the present invention illustrating a cable holding feature for maintaining the fetal spiral electrode in a retracted position.

In addition, untwisted length 16 can be used to fix the position of wire strand 18 (and, hence, fetal spiral electrode 20 to which wire strand 18 is attached) relative to introducer 40 such that fetal spiral electrode 20 is protected inside introducer 40. This is accomplished by locking either a single strand (i.e., wire 26a or 26b) of untwisted length 16 or the entire wire strand 18 under an edge of introducer 40. In this way, fetal spiral electrode 20 is maintained in a recessed position (as shown in FIG. 18) inside introducer 40 before and during the initial stages of use.

2. The Connector

Wire strand 18 terminates in connector 32 (shown in FIGS. 1 and 2) without the need for a strain relief element. Connector 32 has two, main components: a larger diameter grip 44 and a smaller diameter plug 48. Individual wires 26a and 26b are separately connected to ring contacts 34 and 36 in plug 48 of connector 32. Ring contacts 34 and 36, which are separated by spacer 38 and may be gold-plated to resist corrosion, have grooves to facilitate mechanical and electrical connection to mating barrel contacts in support plate 70 upon insertion of plug 48 of connector 32 into an opening of support plate 70 (shown in FIG. 2). Moreover, tip 42 of connector 32 abuts a wall in support plate 70 to prevent over-insertion of connector 32.

Figure 15A:
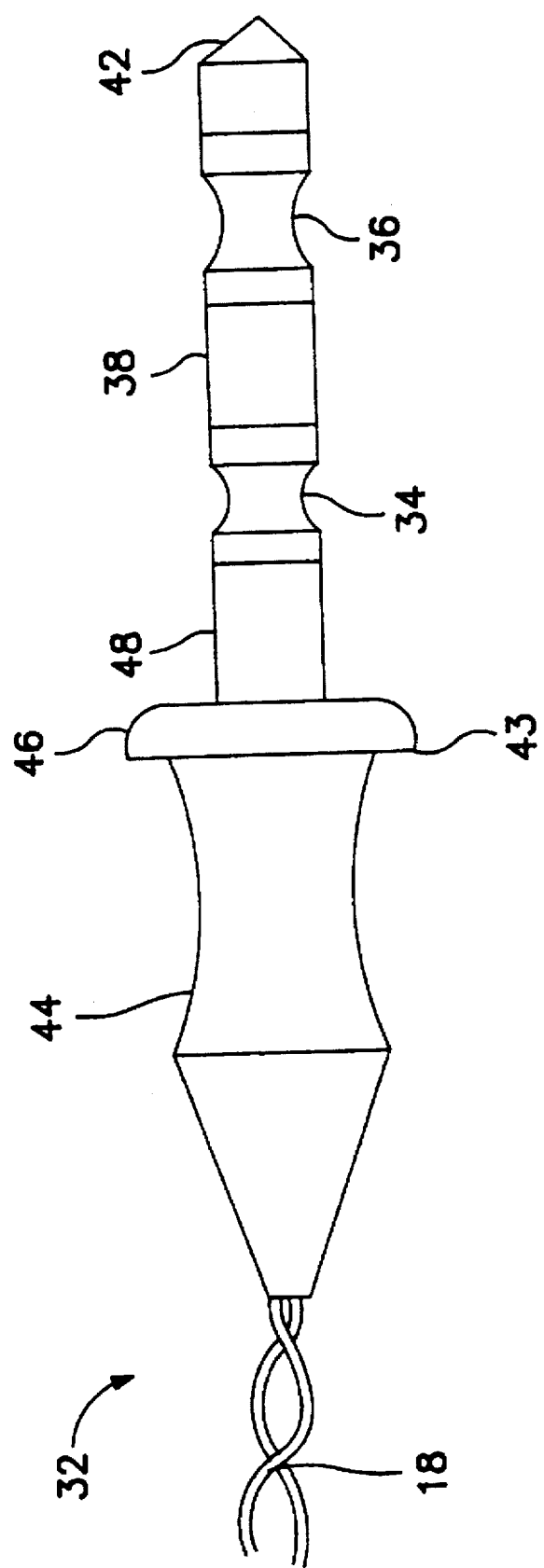
FIGS. 15a, 15b, 15c, 15d, 15e, 15f, 15g, and 15h are side views of various exemplary embodiments of the connector grip in accordance with the present invention.
Figure 15B:
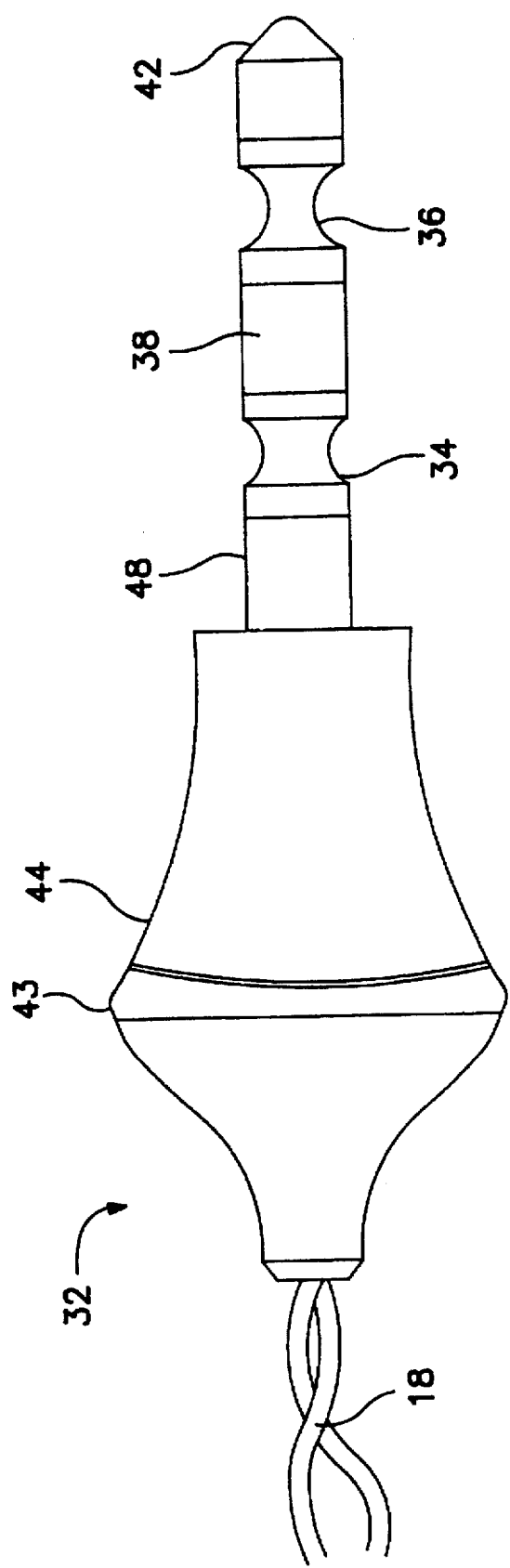
Figure 15C:
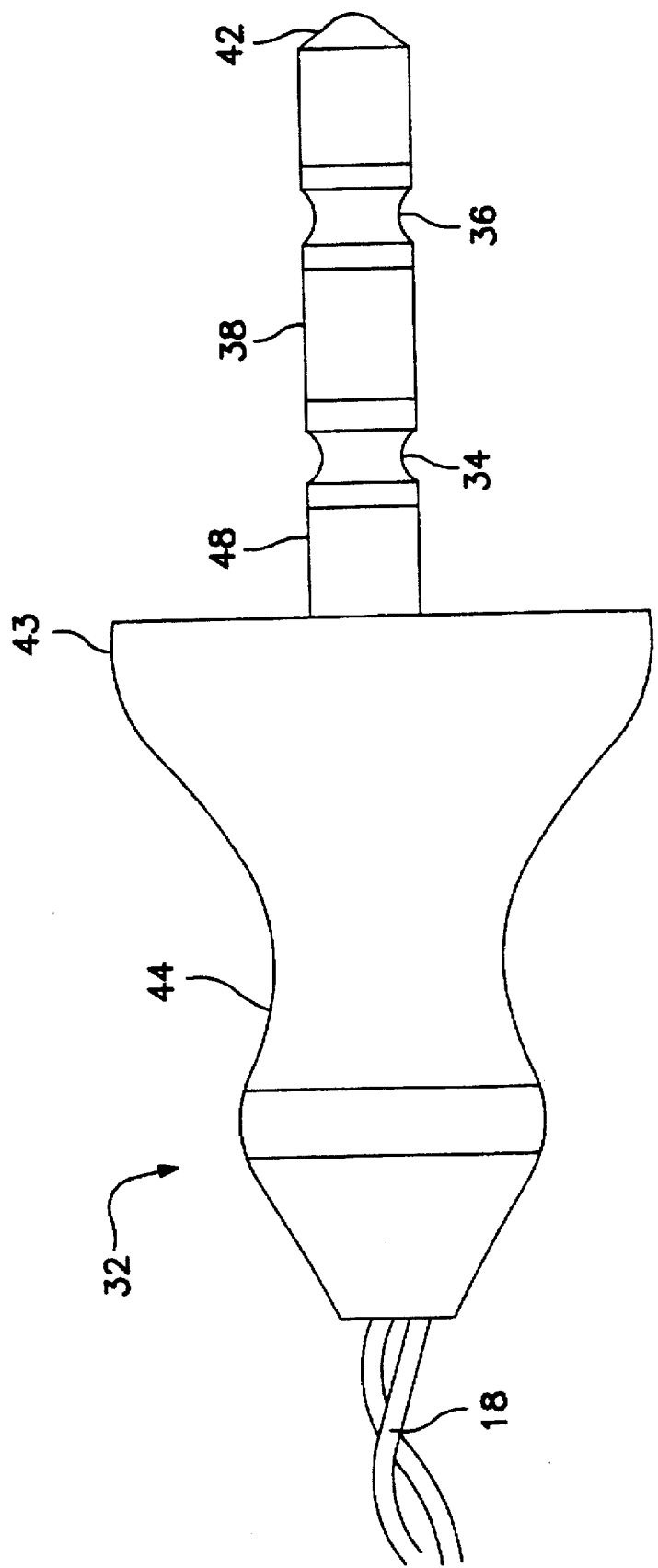
Figure 15D:
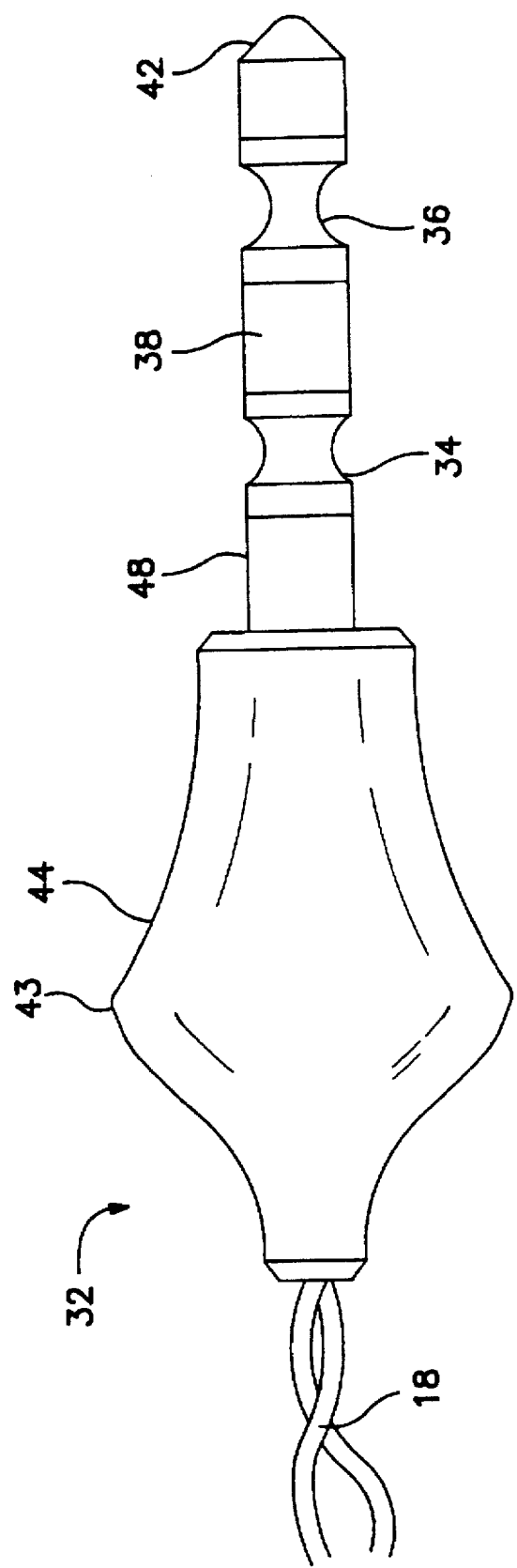
Figure 15E:
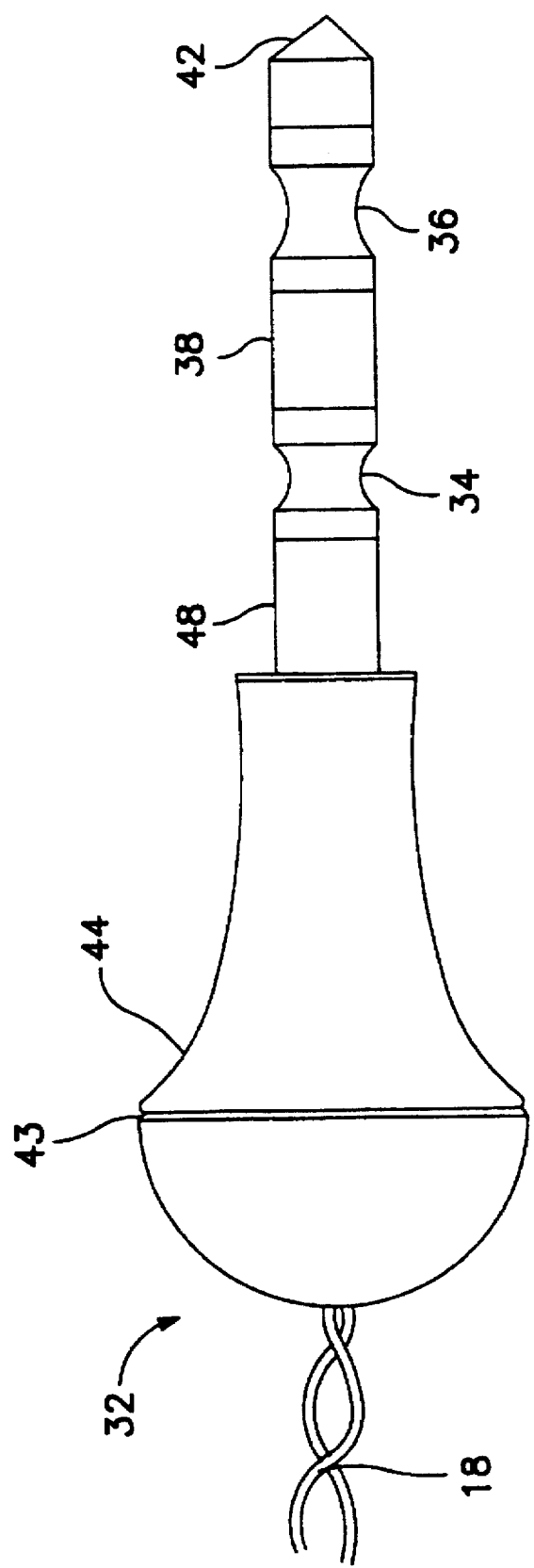
Figure 15F:
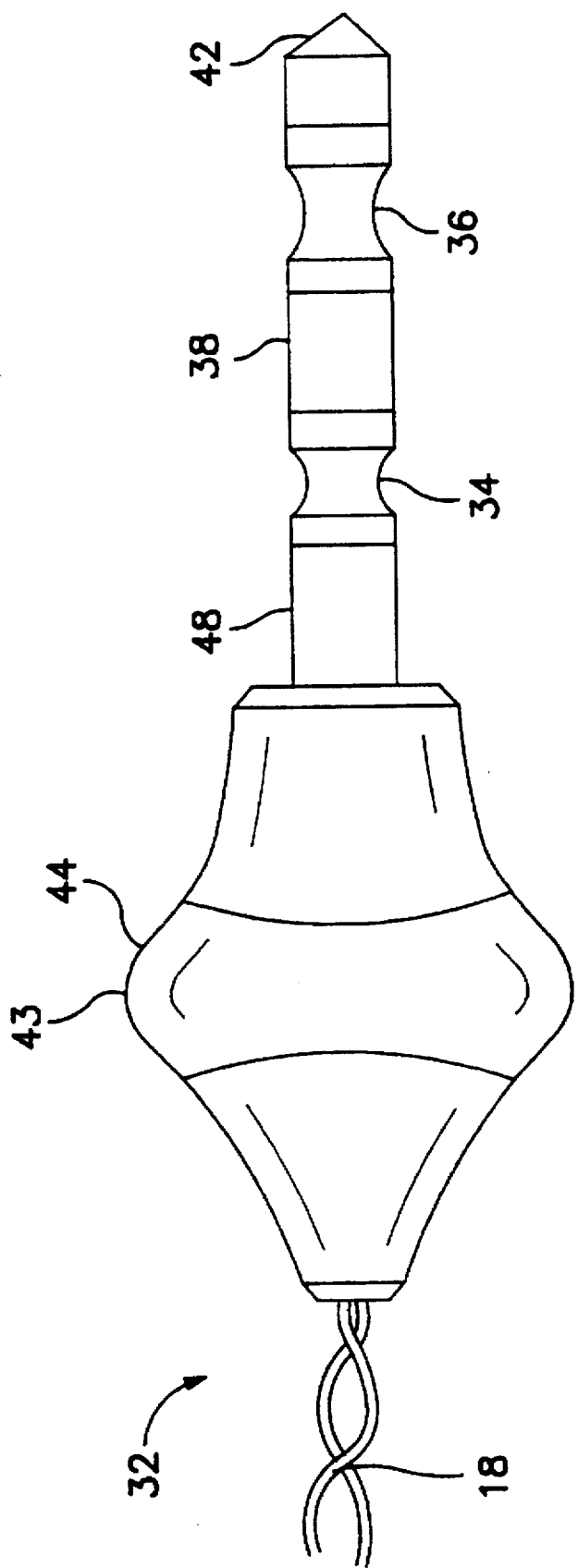
Figure 15G:
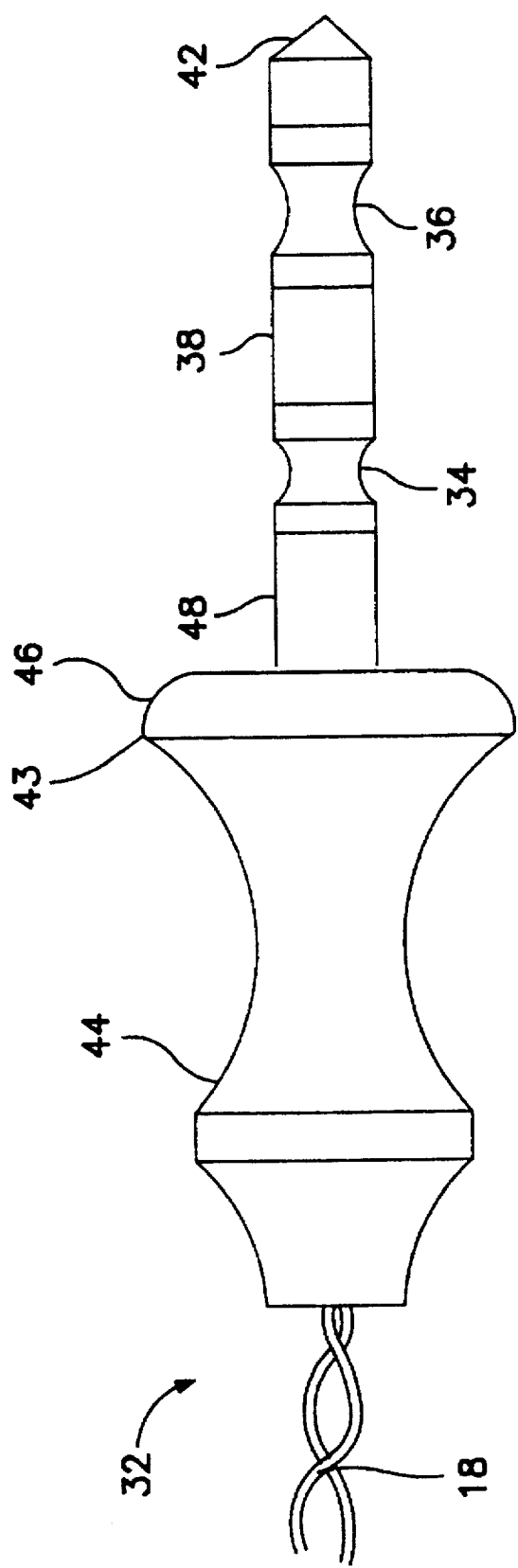

Grip 44 of connector 32 has a diameter sufficiently large to insure that it cannot pass through introducer 40. Specifically, the maximum diameter 43 of grip 44 is larger than the inner diameter of introducer 40. Grip 44 also has an ergonomically designed shape to permit the user to grasp it easily and to insure a proper, sealed connection of connector 32 to support plate 70. Examples of such grip designs are shown in FIGS. 15a through 15h. FIGS. 15a, 15b, 15f, and 15g show grip designs which provide for enhanced ease of pushing and pulling of connector grip 44. Alternatively, FIG. 15c shows an example of a design for grip 44 which focuses on enhancing the ease with which connector 32 can be pushed while FIGS. 15d and 15e show examples of grip designs which focus on enhancing the ease with which connector 32 can be pulled.

Figure 15H:
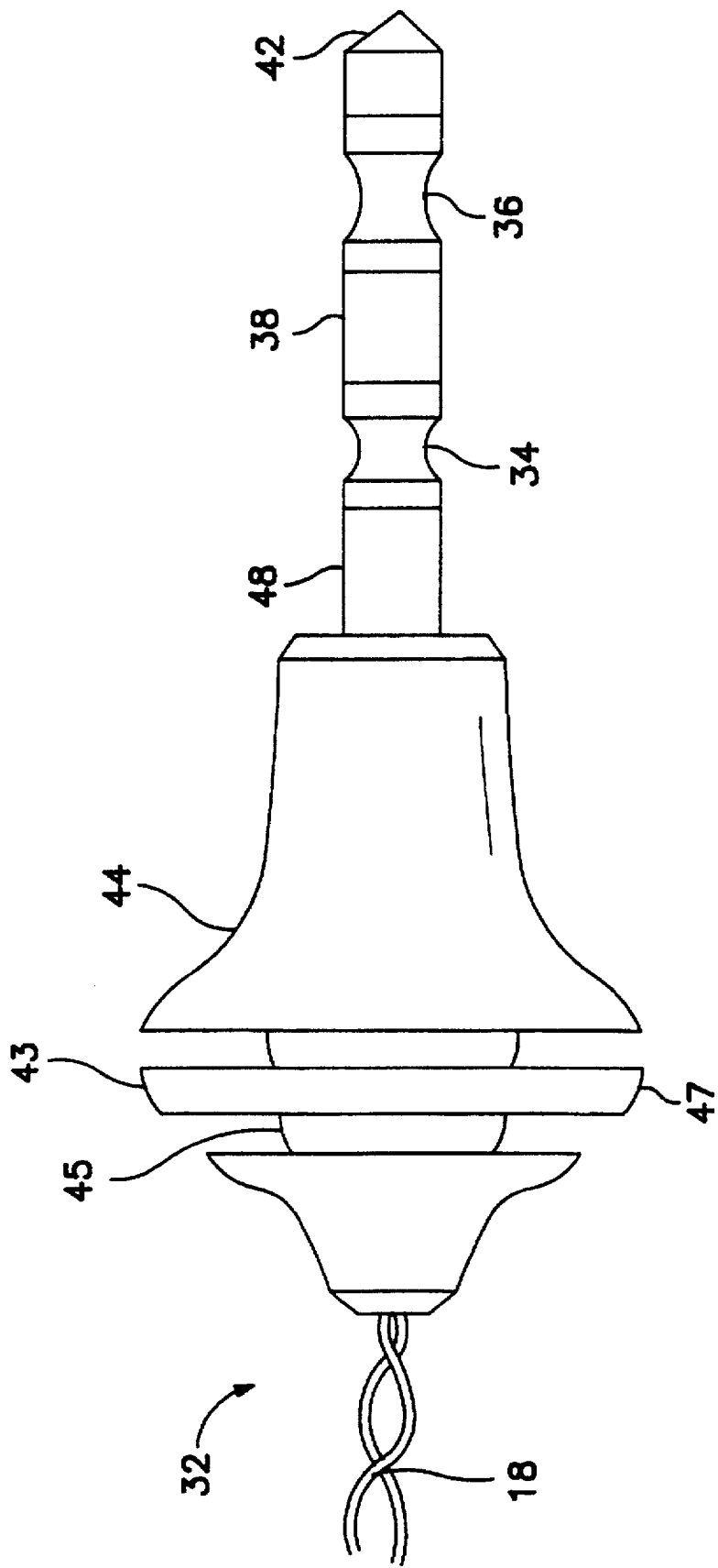
Figure 15J:
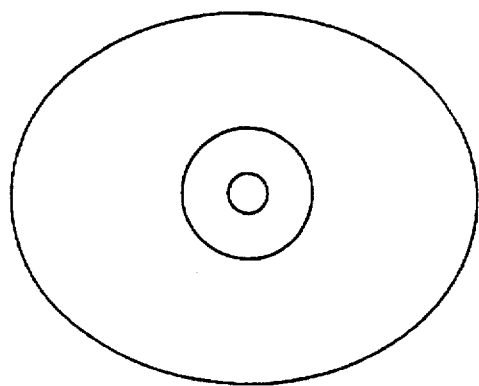
FIGS. 15i, 15j, 15k, and 15l, are various cross-sectional views of exemplary connector grips in accordance with the present invention.
Figure 15L:
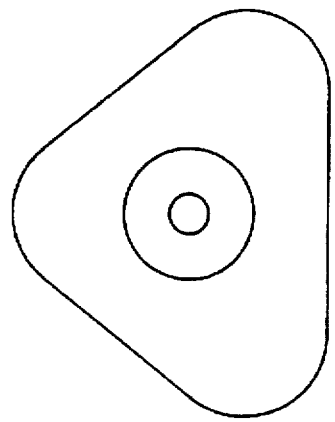

FIG. 15h shows a design of a segmented connector grip 44 having a center core 45, through which wire strand 18 passes, and at least one thin segment 47 which can be flexible or rigid. This segmented grip design can be incorporated in any of the grip designs illustrated in FIGS. 15a through g. The design offers the advantages of a reduction in connector weight and an increase in both flexibility and the ability to grasp and handle (i.e., improved tactility).

Because introducer 40 does not pass over grip 44 during removal of introducer 40, maximum diameter 43 of connector grip 44 is not limited. Wire strand 18 is removed radially through slot 41 in introducer 40 before or as introducer 40 is withdrawn. Thus, the larger diameter of grip 44 of connector 32, which can only be accommodated by a slotted introducer 40, renders connector 32 easy to handle—especially with gloved hands.

Grip 44 can optionally include a larger diameter shoulder ring 46 (i.e., larger than the outer diameter of introducer 40) to insure that connector 32 does not pass through introducer 40. Shoulder ring 46 forms an abrupt transition (typically 90 degrees) with the longitudinal surface of connector 32. In addition, the width of shoulder ring 46, which is relatively inflexible, is approximately 1.5 mm (0.060 inches).

Figure 15I:
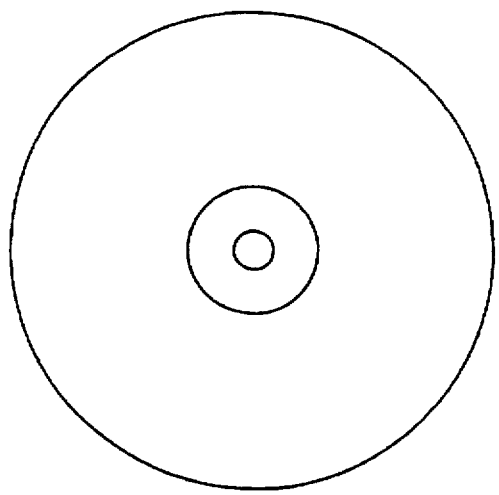
Figure 15K:
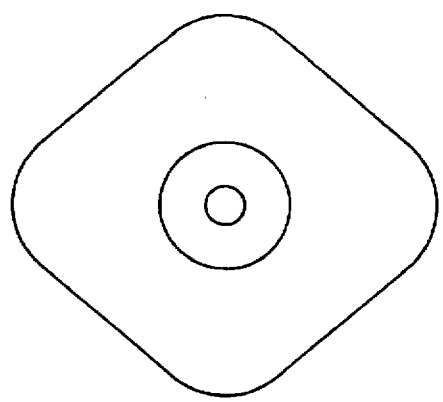

Examples of various cross-sections suitable for grip 44, either with or without shoulder ring 46, are shown in FIGS. 15i (cylindrical), 15j (oval or elliptical), 15k (diamond or parallelogram), and 15l (rounded triangle). These designs can be used with any of the grip designs discussed above. Shoulder ring 46 facilitates grasping of connector 32 while insuring a proper, sealed connection of connector 32 to the support plate 70.

If desired, grip 44 can be smaller than the inside diameter of introducer 40 if grip 44 is provided with a larger diameter shoulder ring 46 which prevents connector 32 from passing through introducer 40. Whether the enlarged grip or shoulder ring 46 is used, the maximum diameter of grip 44 must be sufficient to prevent connector 32 from passing through introducer 40. The length of smaller diameter plug 48 is selected to correspond to the length by which connector 32 must be inserted fully into support plate 70 to assure optimal signal quality. Thus, connector 32 permits a visual indication of full attachment of connector 32 to support plate 70.

For purposes of example only, plug 48 has a length of about 20 mm (0.8 inches) and a diameter of about 3 mm (0.12 inches). Grip 44 has a length of about 18 mm (0.70 inches) and a minimum diameter of about 5 mm (0.20 inches). Maximum diameter 43 of connector grip 44 (or, if shoulder ring 46 is used, the diameter of shoulder ring 46) is about 8.125 mm (0.32 inches). Thus, connector 32 has a total length of about 38 mm (1.5 inches), a minimum diameter of about 5 mm (0.20 inches), and a maximum diameter of about 8.125 mm (0.32 inches).

As discussed in greater detail below, introducer 40 has an outside diameter of about 7.9 mm (0.31 inches), an inner diameter of about 6 mm (0.238 inches), and a wall thickness of about 0.9 mm (0.036 inches). Thus, the maximum diameter of grip 44 of connector 32 is typically 0.25 mm (0.01 inches) greater than the outside diameter of introducer 40 and 2.0 mm (0.08 inches) greater than the inside diameter of introducer 40. These geometries allow grip 44 to seat on the rearward end 92 of introducer 40, preventing connector 32 from entering introducer 40 and wedging introducer 40 apart along slot 41. In fact, tests conducted on the combination of connector 32 and introducer 40 having the dimensions specified above showed that connector 32 did not enter introducer 40.

Figure 10A:
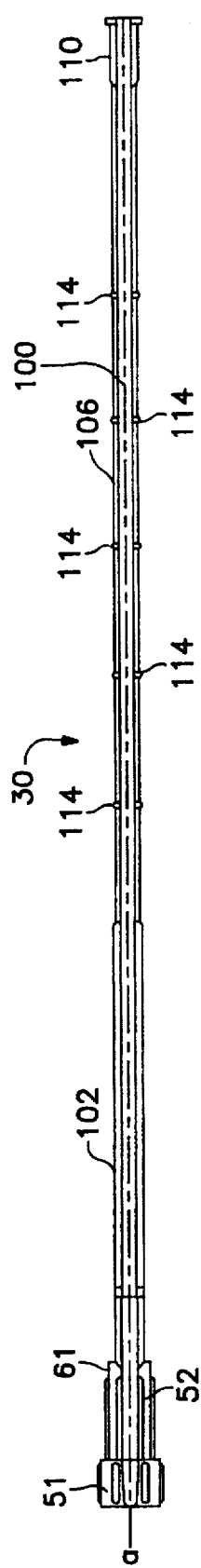
FIG. 10a is a top view of a second embodiment of the drive mechanism, substantially as shown in FIGS. 3–5, but including chamfered or beveled edges on the shoulder of the handle.

Connector 32 as described above and illustrated in the drawing meets the four, main design criteria for a connector: low cost, ease of manufacture, optimal functional performance, and ease of handling. Discussion turns now to the integral, molded components of drive mechanism 12: drive rod 30, clutch 28, and handle 50. The drawing illustrates two, alternative embodiments for drive handle 50. FIGS. 4a and 5 illustrate the first embodiment; FIG. 10a depicts the second embodiment of handle 50.

As shown disposed along longitudinal axis "a" in FIGS. 4a, 4b, 5, and 10a, the length of drive mechanism 12 is about 300 mm (11.8 inches). Drive mechanism 12 is made of polyethylene (high or low density). Polypropylene is also suitable. The combination of structural and flexural modulus in drive mechanism 12 is important to assure that drive mechanism 12 delivers the torque necessary to rotate fetal spiral electrode 20 and provides the "feel" required to assure that fetal spiral electrode 20 is attached to the fetus without over-rotation.

3. The Drive Rod

Drive rod 30 is shown in FIGS. 4a, 4b, 5, and 10a. Introducer 40 must be able to bend at least 45°, and preferably 90°, relative to longitudinal axis "a", to transit the cervix and place fetal spiral electrode 20 into position against the fetus. Drive rod 30 must bend similarly when positioned inside introducer 40. Because drive rod 30 is solid and is not an annular tube, the material chosen for drive rod 30 must assure sufficient flexibility.

Drive rod 30 has three, separate regions along its length to accommodate the variously curved shape of introducer 40. Specifically, the first region 102 adjacent and integral with handle 50, where the minimum drive rod bending exists because introducer 40 is relatively straight in this area, has an outer diameter 104 (about 5.5 mm or 0.22 inches) only slightly less than the inner diameter of introducer 40 (about 6 mm or 0.238 inches). See FIGS. 6 and 9. The second, central region 106, where the drive rod bending is maximum, has a smaller outer diameter 108 (about 4 mm or 0.16 inches) rendering drive rod 30 more flexible. See FIGS. 8 and 9. Central region 106 is about 165 mm (6.5 inches) long. Finally, a short region 110 adjacent clutch 28 is provided with an intermediate outer diameter 112 (about 5 mm or 0.20 inches). See FIGS. 7 and 9. Short region 110 is about 12.5 mm (0.5 inches) long.

Drive rod 30 has a channel 100 which runs longitudinally along its entire length. Channel 100 is sized, having a radius of about 1.2 mm (0.05 inches) and a top opening of about 2.4 mm (0.10 inches), to permit wire strand 18 to exit drive rod 30 through channel 100 when drive rod 30 is removed from introducer 40. Wire strand 18 has an outer diameter of about 2 mm (0.08 inches). Thus, wire strand 18 slips out of channel 100 without the need for radial expansion of drive rod 30. The depth of channel 100 is sufficient, however, to prevent wires 26a and 26b from exiting channel 100 when drive rod 30 is inside introducer 40.

Central region 106 of drive rod 30 has a number of journals 114 spaced, at intervals of about 25 mm (1 inch), along its length. Journals have a length of about 1 mm (0.04 inches) and an outer diameter approximately equal to diameter 112 of short region 110 (about 5 mm or 0.20 inches). See FIG. 10a. Thus, the diameter of journals 114 is larger than diameter 108 of central region 106.

As shown in FIG. 9, journals 114 have a height sufficient so that wire strand 18, when placed in channel 100, is tangent to the outer diameter of journals 114. The geometrical relationship between journals 114 and the depth of channel 100 provides a simulated cylinder for uniform contact between wires 26a and 26b and the inside wall of introducer 40. Consequently, smooth, low-friction rotation of drive rod 30 in introducer 40 is assured regardless of the bend angle assumed by introducer 40. This is especially important in central region 106 of drive rod 30 where the bend of introducer 40 and drive rod 30 is most pronounced.

Journals 114 each have a notch which corresponds to the width of top opening of channel 100. Removal of drive rod 30 must be accomplished without tugging on wire strand 18. Therefore, the ends of the notches in journals 114 are provided with a radius or chamfer to eliminate sharp edges which might catch wires 26a and 26b as they exit channel 100 of drive rod 30. Untwisted length 16 of wire strand 18 should not be provided along the length of wire strand 18 which must exit channel 100 of drive rod 30; wire strand 18 will exit channel 100 more easily than an untwisted pair of individual wires.

The drive rods 30 illustrated in the drawing are examples only. The number of regions provided in forming guide rod 30, the diameters of those regions, and the number of journals 114—all might be varied. The maximum outer diameter of drive rod 30 is about 5.5 mm (0.225 inches). As shown in FIGS. 13 and 14, this diameter assures a clearance 132 of about 0.025 mm (0.001 inches) between drive rod 30 and introducer 40 at the smallest statistically projected inside dimension of 0.226 inches when introducer 40 is bent at an angle, alpha, of about 45°.

Drive rod 30 transmits torque between handle 50 and clutch 28. The variable shaft flexibility provided by the various regions of drive rod 30 enhances both the ability of the user to push, pull, and rotate drive mechanism 12 and the "feel" of drive mechanism 12 relative to conventional devices containing shafts of uniform rigidity throughout. The various regions of drive rod 30 are designed to control the torque versus angular deflection characteristics of drive rod 30 and, hence, of drive mechanism 12.

4. The Clutch

As shown in FIG. 4a, drive rod 30 blends into and is integral with clutch 28. A ramp 120 is provided in the transition area between drive rod 30 and clutch 28. Wire strand 18 rests on ramp 120 as it travels from channel 100 (which is above the center-line of drive mechanism 12 in central region 106 of drive rod 30) to the center of clutch 28 where it engages reference electrode 22.

Figure 17:
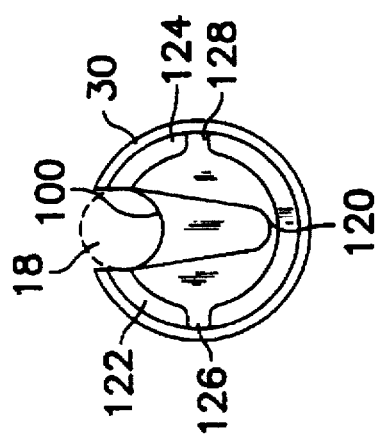
FIG. 17 is an end view of the clutch illustrated in FIG. 16.
Figure 16:
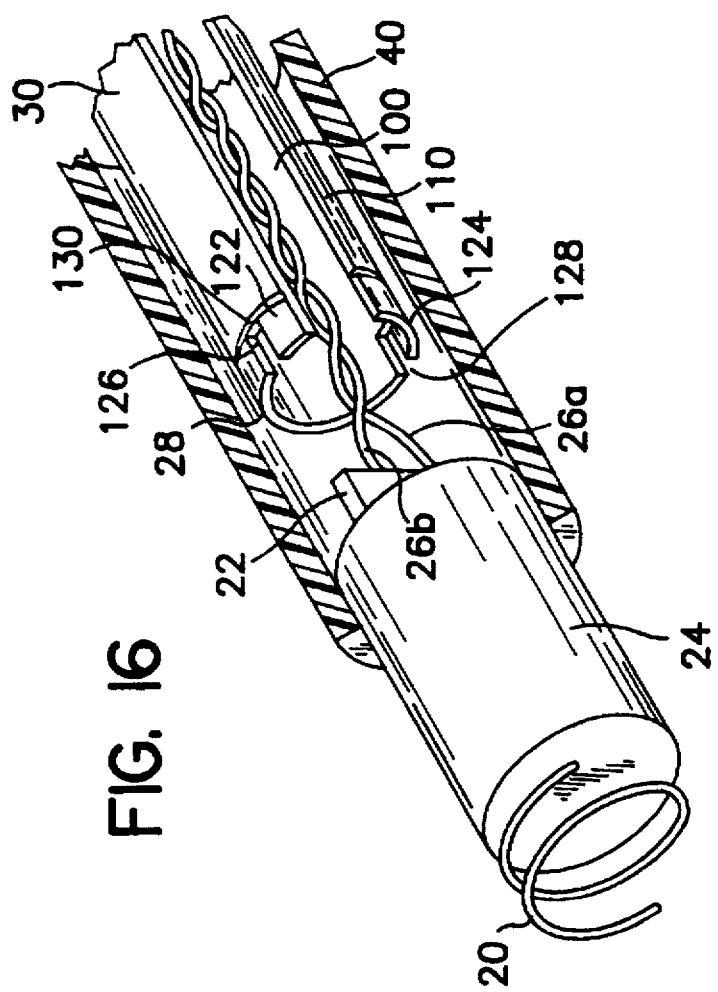
FIG. 16 is a perspective view of the clutch of the fetal spiral electrode system in accordance with the present invention.

FIGS. 16 and 17 best illustrate clutch 28. Clutch 28 has a pair of arms 122 and 124 which define slots 126 and 128. Arms 122 and 124 releasably engage fin-shaped maternal electrode 22, in slots 126 and 128, and center electrode 22 upon engagement. Clutch 28 transmits torque between drive rod 30 and holder 24.

The connection between slots 126 and 128 and electrode 22 is relatively "loose" so that arms 122 and 124 will slip and deflect when holder 24, to which electrode 22 is mounted, meets with a relatively slight amount of resistance to rotation. This occurs when fetal spiral electrode 20 has pierced the fetal epidermis and the front face of holder 24 has contacted the fetus. Continued rotation of handle 50 once resistance has occurred will cause arms 122 and 124 to slip and deflect over electrode 22 and prevent transmission of rotation from handle 50 and drive rod 30 to holder 24 and fetal spiral electrode 20. This loose driving connection is accomplished by making arms 122 and 124 of clutch 28 between slots 126 and 128 soft or pliable enough to allow arms 122 and 124 to bend and slip over electrode 22 when holder 24 resists rotation.

The length of arms 122 and 124 and, correspondingly, the depth of slots 126 and 128 is about 2.5 mm (0.1 inches). Therefore, slots 126 and 128 can fully receive maternal electrode 22 which protrudes out of holder 24 by about 2 mm (0.08 inches). A rim 130 is provided on clutch 28, at the junction between clutch 28 and short region 110 of drive rod 30, for guidance of drive mechanism 12 in introducer 40.

Clutch 28 will disengage maternal electrode 22 after complete engagement of fetal spiral electrode 20. Thus, clutch 28 is designed to disengage maternal electrode 22 in a relatively narrow range of torque. Clutch 28 gives drive mechanism 12 a protective mechanism, allowing drive mechanism 12 to transmit a torque sufficient to affix fetal spiral electrode 20 to the fetus and to slip, or disengage, if a larger torque is applied.

5. The Handle

Figure 10B:
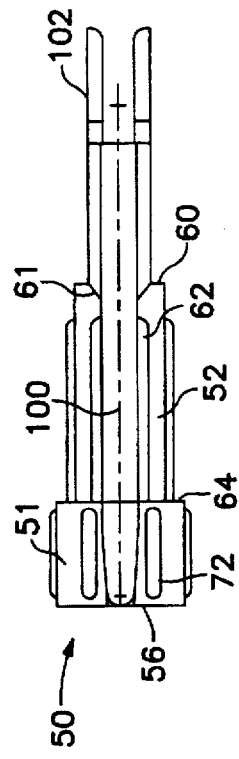

Two alternative embodiments of handle 50 are shown in the drawing. The first embodiment, without a chamfer, bevel, or radius on shoulder 60, is shown in FIGS. 4a, 4b, and 5. FIGS. 10a and 10b show a second embodiment of handle 50 which has a shoulder 60 with beveled, radiused, or chamfered edges 61 to prevent the forward section 52 of handle 50 from catching on slot 41 in introducer 40 when handle 50 is rotated relative to introducer 40. A 45° angle is suitable for beveled edges 61.

In both embodiments, handle 50 is attached to and integral with first region 102 of drive rod 30. An incline 140 is provided in handle 50. Preferably, the angle of inclination, beta, between the center line of drive mechanism 12 and incline 140 is about 4°. Wire strand 18 rests on incline 140 as it travels from channel 100 (which is above the center-line of drive mechanism 12 in first region 102 of drive rod 30) to locking slit 58 in end 56 of handle 50 (see FIG. 3) where wire strand 18 exits handle 50. Incline 140 slopes downward from channel 100 to slit 58. Thus, wire strand 18 is recessed in drive rod handle 50 and, because recessed, is less likely to catch on introducer 40 as handle 50 is rotated relative to introducer 40.

As shown in FIGS. 4a, 4b, 5, 10a, and 10b, handle 50 has two cylindrical sections: a rearward section 51 and a forward section 52. Locking slit 58 extends through end 56 of handle 50 (see FIG. 3). Locking slit 58 tapers into a deep "V" or "U" shape from its top at channel 100 to its bottom about 3 mm from the edge of end 56 of handle 50. Locking slit 58 has a maximum width of about 1 mm (0.04 inches) at its bottom. Wire strand 18 may be wedged in flexible locking slit 58 (which expands to snugly hold wire strand 18) to fix wire strand 18 (and, hence, fetal spiral electrode 20 on the end of wire strand 18) in position.

Forward section 52 of handle 50 has an outer diameter (7.1 mm or 0.28 inches) which is larger than the inner diameter of introducer 40. Thus, forward section 52 provides shoulder 60 to limit the forward movement of drive rod 30 inside introducer 40. The respective lengths of drive rod 30, introducer 40, and forward section 52 are selected so that fetal spiral electrode 20 extends about 9 mm (0.35 inches) outside the forward end 90 of introducer 40 when first region 102 of drive rod 30 is fully mounted inside the rearward end 92 of introducer 40 (such that shoulder 60 abuts rearward end 92 of introducer 40). Forward section 52 has ribs 62 to facilitate handling of drive mechanism 12 when attaching fetal spiral electrode 20 to the fetus.

Figure 19B:
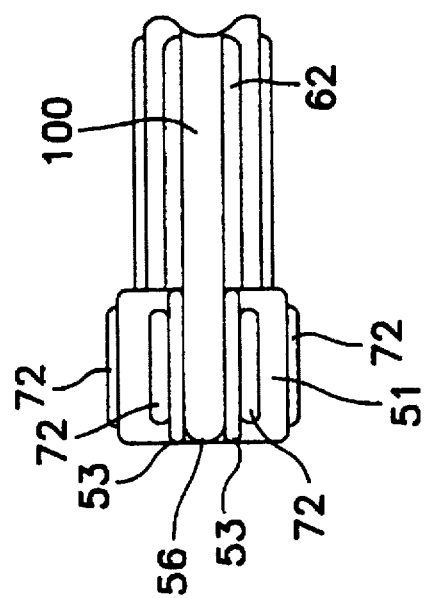
Figure 19A:
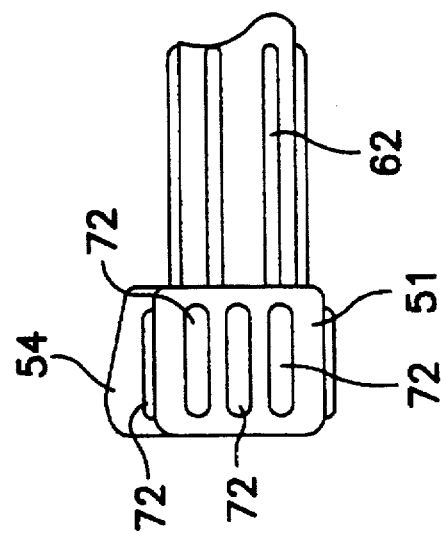
FIG. 19a is a side view of a drive rod handle showing a tactile sensing member located on the rearward section of the handle.

Rearward section 51 of handle 50 is larger in diameter than forward section 52 and forms a ledge 64. Like forward section 52, rearward section 51 of handle 50 has ribs 72 to facilitate handling. FIGS. 19a and 19b illustrate a tactile sensing member 54 integrally incorporated into rearward section 51 of handle 50. Tactile sensing member 54 has two, substantially parallel, raised wall portions 53 disposed on either side of channel 100 in rearward section 51. Wall portions 53 help the user to identify the radial direction in which to pull electrode wires 26a and 26b in order to disengage them from locking slit 58. This feature permits the blind release of wires 26a and 26b by sense of touch, thus obviating the need for the user to look at handle 50 before releasing wires 26a and 26b or to determine the orientation of locking slit 58 (which is parallel to wall portions 53).

Tactile sensing member 54 can also be used as a pointer to inform the user when a complete rotation of fetal spiral electrode 20 has been achieved. Such indication minimizes the risk that fetal spiral electrode 20 will penetrate insufficiently or excessively into the fetal epidermis, which would occur upon insufficient or excessive rotation, respectively, of handle 50. If handle 50 is rotated more than about one or one and a quarter full turns, or beyond the point where slight resistance is felt (indicating that fetal spiral electrode 20 is properly secured to the fetus), fetal spiral electrode 20 may pull out of the fetal scalp tissue and, thus, damage that tissue. In combination, tactile sensing member 54 and pliable arms 122 and 124 of clutch 28 (which bend and slip over electrode 22 when holder 24 resists rotation, as discussed above) help to prevent such damage.

Wire strand 18 travels in channel 100, down incline 140, and through locking slit 58. Wire strand 18 is fixed in position, by a wedging action, in locking slit 58. By holding wire strand 18 in a fixed position in locking slit 58, holder 24 and electrodes 20 and 22 are held against the forward end of drive rod 30. Because holder 24 cannot move away from drive rod 30 while wire strand 18 is secured in locking slit 58, engagement is facilitated between fin-shaped reference electrode 22 and clutch 28 of drive mechanism 12 during application of fetal spiral electrode 20.

Locking slit 58 also provides the added advantage that wire strand 18 can be maintained in channel 100 throughout the process of attaching fetal spiral electrode 20 to the fetus, thereby preventing wires 26a or 26b from catching on the adjacent edges of introducer 40. This is accomplished by applying tension to wire strand 18 before forcing it into locking slit 58. This tension is applied by bowing central region 106 of drive rod 30 as shown in FIG. 4b and pulling wire strand 18 taut before wedging wire strand 18 in locking slit 58. Drive rod 30 is then inserted into introducer 40 while insuring that drive rod channel 100 is located opposite (i.e., not in line with nor open to) slot 41 in introducer 40 (see FIG. 14) such that wire strand 18 is recessed in channel 100 and is prevented from protruding through slot 41 in introducer 40.

Handle 50 and drive rod 30 are molded together as part of integral drive mechanism 12. When the user rotates handle 50, therefore, drive rod 30 automatically rotates along with handle 50. Consequently, holder 24 and fetal spiral electrode 20 also rotate. The pressure fit of the conventional two-piece drive mechanism, which may inadequately transmit rotational motion between the handle and the drive tube (risking slippage), is avoided.

The integrally molded, single-piece drive mechanism 12 of the present invention provides the user with consistent and optimal tactile feedback. The user turns handle 50 until a mild resistance is felt. Such resistance indicates that fetal spiral electrode 20 has been securely attached to the fetus. Because there can be no slippage between handle 50 and drive rod 30, as is possible with the conventional, two-piece drive mechanism, the user will receive the tactile feedback desired. Consequently, the user can be confident that a secure attachment of fetal spiral electrode 20 has been achieved.

6. The Introducer

As illustrated in FIG. 11, introducer 40 is a curved, form-sustaining member of adjustable shape for insertion of fetal spiral electrode 20 through the mother's cervix and into contact with the fetus during labor. Drive mechanism 12, holder 24, and wire strand 18 are rotatably and slidably disposed within introducer 40. As shown disposed along longitudinal axis "a" in FIG. 13, introducer 40 has a length of about 270 mm (10.6 inches), a substantially uniform outer diameter of about 0.31 inches (7.9 mm), and a substantially constant wall thickness of about 0.036 inches (0.9 mm).

Introducer 40 may be shaped, as shown in FIG. 13, with a gentle curve to conform comfortably with the shape of the vagina and cervix of a woman in labor. Introducer 40 can be manufactured via a standard extrusion process. Introducer 40 may be extruded or injection molded and formed from a polyolefin such as high-density polyethylene. Any material which is flexible, form-sustaining, and compatible with insertion into the body is suitable for introducer 40.

Introducer 40 has a longitudinal slot 41, an open forward end 90, and an open rearward end 92. Such a design is consistent with the '957 patent. Distinguish introducer 40 from a guide tube having a slit. Longitudinal slot 41 is sufficiently wide to permit easy removal of wires 26a and 26b from introducer 40 once fetal spiral electrode 20 has been placed. A "slit" guide tube does not have any space in the resting position; the slit guide tube forms a completed, closed tube in the resting position. In contrast, introducer 40 has a space—slot 41—forming a "C"-shape, in the resting position (see the cross section of introducer 40 shown in FIG. 12).

Slot 41 is about 0.1 inches (2.5 mm) wide. The width of slot 41 in introducer 40 is larger than the diameter of wire strand 18 to enable easy removal of wire strand 18 from slot 41. Because introducer 40 has longitudinal slot 41 disposed along its entire length, introducer 40 can be removed and discarded once fetal spiral electrode 20 is engaged with the presenting part of the fetus.

Forward end 90 of introducer 40, which contacts the fetus, is provided with a radius, bevel, or first chamfer 94 on both sides of slot 41. First chamfer 94 assures that forward end 90 does not have any sharp edges. Thus, first chamfer 94 helps to prevent harm or injury to the fetus and maternal tissue when introducer 40 makes contact. Rearward end 92 of introducer 40 can also be provided with a radius, bevel, or second chamfer 96 on either or both sides of slot 41. Second chamfer 96 helps to prevent forward section 52 of handle 50 from catching on slot 41 in introducer 40 when handle 50 is rotated. Second chamfer 96 can also be used to facilitate holding wire strand 18 as described below.

7. Cable-Holding Feature

As shown in FIG. 18, introducer 40 also has a cable holding feature. The cable holding feature prevents fetal spiral electrode 20 from protruding from introducer 40 during storage and before use. At least one wire 26a and 26b of untwisted length 16 of wire strand 18 is wedged between the inner diameter of introducer 40 and the outer diameter 104 of first region 102 of drive rod 30. Second chamfer 96 on rearward end 92 of introducer 40 (i.e., the end opposite forward end 90 which contacts the fetus) helps to position the wire or (if the entire wire strand 18 is to be wedged) wires. Then introducer 40 is rotated such that the wire or wires of untwisted length 16 is or are wedged snugly between the inner diameter of introducer 40 and outer diameter 104 of first region 102 of drive rod 30.

In this manner, a predetermined distance is maintained between shoulder 60 of handle 50 and rearward end 92 of introducer 40 during storage and handling of fetal spiral electrode system 10 before and during the initial stages of use. This predetermined distance is selected to assure that first region 102 of drive rod 30 is not mounted completely inside introducer 40. By maintaining this predetermined distance, however, drive rod 30 is retracted far enough inside introducer 40 so that holder 24 and fetal spiral electrode 20 are retained in a protected position inside introducer 40. Moreover, locking slit 58 secures wires 26a and 26b so that holder 24 is held in clutch 28 and against the forward end of drive rod 30. Because at least one wire of untwisted length 16 is wedged between drive rod 30 and introducer 40, relative motion between the two is effectively prevented and drive rod 30 cannot slip out of introducer 40 accidentally during handling.

C. Use of the Present Invention

During storage, wire strand 18 is wedged in locking slit 58. At least one wire of untwisted length 16 of wire strand 18 is wedged between introducer 40 and drive rod 30, holding fetal spiral electrode 20 retracted in introducer 40. Thus, fetal spiral electrode 20 is protected and will not harm those who handle fetal spiral electrode system 10.

To use fetal spiral electrode system 10 of the present invention, the shape of introducer 40 is adjusted and introducer 40 is inserted through the mother's cervix and into contact with the fetus. Drive rod 30 is freed for longitudinal and rotational movement within the introducer 40 by releasing the wedged wire strand 18. Release is accomplished by pulling wire strand 18 out from between introducer 40 and drive rod 30. Fetal spiral electrode 20 is still in its retracted position within introducer 40.

Next, drive rod 30 is pushed by applying a forward force to handle 50 to move drive rod 30 through introducer 40, without rotation, until fetal spiral electrode 20 contacts the fetus. (There is no need to pull back on drive rod 30 to release a safety tab as for certain known devices.) Contact will occur just before rearward end 92 of introducer 40 would contact shoulder 60 of handle 50. Clutch 28 engages fin-shaped reference electrode 22 and, accordingly, holder 24 and fetal spiral electrode 20 will move forward in introducer 40 as drive rod 30 does so.

While pressure is maintained against the fetus with both introducer 40 and drive rod 30, drive rod 30 is rotated (in a clockwise direction), using handle 50, until fetal spiral electrode 20 is secured to the fetal epidermis. Typically, one full revolution suffices to secure fetal spiral electrode 20. Locking slit 58, tactile sensing device 54, or both (if both features are provided), can be used as a pointer to inform the user when a complete rotation of fetal spiral electrode 20 has been achieved.

Once fetal spiral electrode 20 is secured to the fetus, the user slides wire strand 18 out of locking slit 58 and slides drive mechanism 12 (including drive rod 30) completely out of introducer 40 and out of the mother by pulling handle 50. There is no need to completely straighten wire strand 18 before drive mechanism 12 is removed. Wires 26a and 26b will automatically and laterally slide from channel 100 as drive mechanism 12 is pulled out. Subsequently, the user removes introducer 40 with electrode wires 26a and 26b sliding radially out of introducer 40. Introducer 40 never passes over connector 32. This leaves electrodes 20 and 22, holder 24, and wires 26a and 26b in place inside the mother.

Finally, connector 32 is plugged into support plate 70 using grip 44. Connector 32 is pushed into support plate 70 until shoulder ring 46 contacts the surface of support plate 70, indicating that connector 32 is fully inserted. Simultaneously, tip 42 of connector 32 will abut a wall in support plate 70 to prevent over-insertion of connector 32. Insertion of connector 32 in support plate 70 connects electrodes 20 and 22 to monitor 78.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. The integrated introducer and drive rod system in accordance with the present invention can be used, for example, to attach spiral-shaped, biological needle probes other than the fetal spiral electrode shown in the '990 patent. Because a fetal spiral electrode is the preferred version of the probe, however, the system is illustrated incorporating such an electrode.

What is claimed:

1. A fetal electrode product for transmitting signals indicative of fetal heart rate from a fetus inside a mother to a monitor external to the mother, said product comprising:

a holder having a fetal spiral electrode on one end and a maternal reference electrode on its opposite end;

a twisted wire strand including a pair of wires each having a first end and a second end, said first ends of said wires respectively connected to said fetal spiral electrode and said maternal reference electrode;

a solid drive mechanism disposed along a longitudinal axis and having:
    (a) a drive rod including a circumference with an outside diameter, a forward end, and a rearward end,
    (b) a handle on said rearward end of said drive rod imparting translation and rotation to said drive rod,
    (c) a clutch on said forward end of said drive rod imparting translation and rotation to said holder to secure attachment of said fetal spiral electrode to the fetus, and
    (d) a channel longitudinally disposed in said drive mechanism and transporting said twisted wire strand from said fetal spiral electrode and said maternal reference electrode through said handle;

an introducer disposed arm rod at least a portion of said drive mechanism and adapted to be comfombly inserted through the cervix of the mother and having:
    (a) an open forward end,
    (b) an open rearward end,
    (c) an inner diameter, within which said holder is slidably and rotatably disposed, only slightly greater than said outside diameter of said drive rod, and
    (d) a longitudinal slot disposed along the entire length of said introducer; and a connector engaging said second ends of said wires of said twisted wire strand and having an outside dimension at least greater than said inner diameter of said introducer so that said introducer cannot be pulled over said connector after said fetal spiral electrode is attached to the fetus, said connector adapted to engage the monitor.

2. The fetal electrode product in accordance with claim 1 wherein said handle has a rearward portion with an end and a forward portion, said forward portion connected to said rearward end of said drive rod, said handle having:
    (a) a locking slit in said end of said rearward portion in a plane transverse to said longitudinal axis of said drive mechanism, said locking slit adapted to securely wedge said twisted wire strand in a fixed position within said locking slit; and
    (b) an incline sloping downward under said channel from said drive rod to said locking slit and transporting said twisted wire strand to said locking slit,
    said channel aligned with said incline and with said locking slit for transporting said twisted wire strand from said fetal spiral electrode and said maternal reference electrode to the monitor.

3. The fetal electrode product in accordance with claim 1 wherein said introducer has at least one of a bevel, a chamfer, and a radius being located at the intersection of said slot with said rearward end of said introducer and preventing said handle from catching on said slot in said introducer when said handle is rotated relative to said introducer.

4. The fetal electrode product in accordance with claim 3 wherein said at least one bevel, chamfer, and radius located at the intersection of said slot with said rearward end of said introducer positions said twisted wire strand, said twisted wire strand wedging between said inner diameter of said introducer and said outside diameter of said drive rod.

5. The fetal electrode product in accordance with claim 1 wherein said introducer has at least one of a bevel, a chamfer, and a radius being located at the intersection of said slot with said forward end of said introducer and preventing harm and injury to the fetus and mother.

6. The fetal electrode product in accordance with claim 1 wherein said connector has a grip facilitating manipulation of said connector and a smaller diameter plug.

7. The fetal electrode product in accordance with claim 6 wherein said grip of said connector has a shoulder ring.

8. The fetal electrode product in accordance with claim 7 wherein said connector has a longitudinal surface and said shoulder ring forms an abrupt transition with said longitudinal surface of said connector.

9. The fetal electrode product in accordance with claim 6 wherein said grip is segmented reducing the weight of said connector and increasing the flexibility and the tactility of said connector.

10. The fetal electrode product in accordance with claim 1 wherein said longitudinal slot disposed along the entire length of said introducer has a width sufficient to permit passage of said twisted wire strand.

11. The fetal electrode product in accordance with claim 10 wherein said slot of said introducer is about 2.5 mm wide.

12. A fetal electrode product for transmitting signals indicative of fetal heart rate from a fetus inside a mother to a monitor external to the mother, said product comprising:

a holder having a fetal spiral electrode on one end and a maternal reference electrode on its opposite end;

a twisted wire strand including a pair of wires each having a first end and a second end, said first ends of said wires respectively connected to said fetal spiral electrode and said maternal reference electrode and said second ends of said wires adapted to be connected to the monitor; and a solid drive mechanism disposed along a longitudinal axis and having;
 (a) a drive rod including a circumference with an outside diameter, a forward end, and a rearward end,
 (b) a handle having a rearward portion with an end and a forward portion, said forward portion connected to said rearward end of said drive rod and imparting translation and rotation to said drive rod, said handle having:
  i) a locking slit in said end of said rearward portion in a plane transverse to said longitudinal axis of said drive mechanism, said locking slit adapted to securely wedge said twisted wire strand in a fixed position within said locking slit; and
  ii) an incline sloping downward from said drive rod to said locking slit and transporting said twisted wire strand to said locking slit,
 (c) a clutch on said forward end of said drive rod imparting translation and rotation to said holder to secure attachment of said fetal spiral electrode to the fetus, and
 (d) a channel longitudinally disposed in said drive mechanism, said channel aligned with said incline and with said locking slit for transporting said twisted wire strand from said fetal spiral electrode and said maternal reference electrode to the monitor.

13. The fetal electrode product in accordance with claim 12 further comprising an introducer disposed around at least a portion of said drive mechanism, adapted to be comfortably inserted through the cervix of the mother and having:
 (a) an open forward end;
 (b) an open rearward end;
 (c) an inner diameter, within which said holder is slidably and rotatably disposed, only slightly greater than said outside diameter of said drive rod; and
 (d) a longitudinal slot disposed along the entire length of said introducer.

14. The fetal electrode product in accordance with claim 13 wherein said handle has at least one of a chamfer, a radius, and a bevel on said forward portion preventing said forward portion of said handle from catching on said slot in said introducer when said handle is rotated relative to said introducer.

15. The fetal electrode product in accordance with claim 14 wherein said handle has at least one of a chamfer and a bevel disposed at an angle of about 45°.

16. The fetal electrode product in accordance with claim 13 wherein said introducer has at least one of a bevel, a chamfer, and a radius located at the intersection of said slot with said rearward end of said introducer and preventing said handle from catching on said slot in said introducer when said handle is rotated relative to said introducer.

17. The fetal electrode product in accordance with claim 12 wherein said handle has a tactile sensing member on said rearward portion of said handle.

18. The fetal electrode product in accordance with claim 17 wherein said tactile sensing member has two substantially parallel raised wall portions disposed on either side of said channel in said rearward portion of said handle permitting blind release of said twisted wire strand from said locking slit.

19. The fetal electrode product in accordance with claim 12 wherein said inlet an angle of about slopes at an angle of about 4°.

20. A fetal electrode product for transmitting signals indicative of fetal heart rate from a fetus inside a mother to a monitor external to the mother, said product comprising:

a holder having a fetal spiral electrode on one end and a maternal reference electrode on its opposite end;

a twisted wire strand including a pair of wires each having a first end and a second end, said first ends of said wires respectively connected to said fetal spiral electrode and said maternal reference electrode and said second ends of said wires adapted to be connected to the monitor;

a solid drive mechanism having a circumference with an outside diameter and imparting translation and rotation to said holder to secure attachment of said fetal spiral electrode to the fetus;

an introducer disposed around at least a portion of said drive mechanism and adapted to be comfortably inserted through the cervix of the mother and having:
 (a) an open forward end,
 (b) an open rearward end,
 (c) an inner diameter, within which said holder is slidably and rotatably disposed, only slightly greater than the outside diameter of said drive mechanism, and
 (d) a longitudinal slot disposed along the entire length of said introducer with at least one of a bevel, a chamber, and a radius being located at the intersection of said slot with said rearward end of said introducer and positioning said twisted wire strand, said twisted wire strand wedging between said inner diameter of said introducer and said outside diameter of said solid drive mechanism.

21. The fetal electrode product in accordance with claim 20 wherein said solid drive mechanism has a drive rod, a handle, and a clutch integrally molded together to form said drive mechanism.

22. The fetal electrode product in accordance with claim 21 wherein said drive mechanism is formed from one of polyethylene and polypropylene.

23. The fetal electrode product in accordance with claim 21 further comprising a ramp between said drive rod and said clutch and an incline between said drive rod and said handle.

24. A fetal electrode product for transmitting signals indicative of fetal heart rate from a fetus inside a mother to a monitor external to the mother, said product comprising:

a holder having a fetal spiral electrode on one end and a maternal reference electrode on its opposite end;

a twisted wire strand including a pair of wires each having a first end and a second end, said first ends of said wires respectively connected to said fetal spiral electrode and said maternal reference electrode;

a solid drive mechanism disposed along a longitudinal axis and having:
(a) a drive rod including a circumference with an outside diameter, a forward end, and a rearward end,
(b) a handle having a rearward portion with an end and a forward portion, said forward portion connected to said rearward end of said drive rod and imparting translation and rotation to said drive rod, said handle including:
  i) a locking slit in said end of said rearward portion in a plane transverse to said longitudinal axis of said drive mechanism, said locking slit adapted to securely wedge said twisted wire strand in a fixed position within said locking slit; and
  ii) an incline sloping downward from said drive rod to said locking slit and transporting said twisted wire strand to said locking slit,
(c) a clutch on said forward end of said drive rod imparting translation and rotation to said holder to secure attachment of said fetal spiral electrode to the fetus, and
(d) a channel longitudinally disposed in said drive mechanism, said channel aligned with said incline and with said locking slit for transporting said twisted wire strand from said fetal spiral electrode and said maternal reference electrode to the monitor;

an introducer disposed around at least a portion of said drive mechanism and adapted to be comfortably inserted through the cervix of the mother and having:
(a) an open forward end,
(b) an open rearward end,
(c) an inner diameter, within which said holder is slidably and rotatably disposed, only slightly greater than said outside diameter of said drive rod, and
(d) a longitudinal slot disposed along the entire length of said introducer with at least one of a bevel, a chamfer, and a radius being located at the intersection of said slot with said rearward end of said introducer and positioning said twisted wire strand, said twisted wire strand wedging between said inner diameter of said introducer and said outside diameter of said drive rod; and a connector engaging said second ends of said wires of said twisted wire strand and having an outside dimension at least greater than said inner diameter of said introducer so that said introducer cannot be pulled over said connector after said fetal spiral electrode is attached to the fetus, said connector adapted to engage the monitor.

* * * * *

UNITED STATES PATENT AND TRADEMARK OFFICE
CERTIFICATE OF CORRECTION

PATENT NO. : 5,671.736
DATED : September 30, 1997
INVENTOR(S) : Pettit et al.

It is certified that error appears in the above-identified patent and that said Letters Patent is hereby corrected as shown below:

On the Cover Page, under References Cited, U.S. Patent Documents, delete "Re.32,294" and insert therefor --Re. 32,204--.

In Col. 1, line 66, insert --(-- before "and,".

In Col. 18, line 14 (Claim 19), delete "inlet an angle of about" and insert therefor --incline of said handle--.

In Col. 18, line 40 (Claim 19), delete "chamber" and insert therefor --chamfer--.

Signed and Sealed this

Thirty-first Day of March, 1998

*Attest:*

BRUCE LEHMAN

*Attesting Officer*      Commissioner of Patents and Trademarks